US010930383B2

(12) United States Patent
Lesau et al.

(10) Patent No.: US 10,930,383 B2
(45) Date of Patent: Feb. 23, 2021

(54) CONNECTED SENSOR SUBSTRATE FOR BLISTER PACKS

(71) Applicant: CUEPATH INNOVATION INC., Vancouver (CA)

(72) Inventors: Victor Gusev Lesau, Vancouver (CA); Ivan Spogreev, Vancouver (CA)

(73) Assignee: CuePath Innovation Inc., Vancouver (CA)

( * ) Notice: Subject to any disclaimer, the term of this patent is extended or adjusted under 35 U.S.C. 154(b) by 169 days.

(21) Appl. No.: 16/148,297

(22) Filed: Oct. 1, 2018

(65) Prior Publication Data

US 2019/0103181 A1 Apr. 4, 2019

Related U.S. Application Data

(63) Continuation-in-part of application No. 15/202,343, filed on Jul. 5, 2016, now Pat. No. 10,089,445.
(Continued)

(51) Int. Cl.
*A61J 1/03* (2006.01)
*G16H 20/13* (2018.01)
(Continued)

(52) U.S. Cl.
CPC .............. *G16H 20/13* (2018.01); *A61J 1/035* (2013.01); *B65D 75/367* (2013.01); *B65D 75/54* (2013.01); *A61J 7/0418* (2015.05); *A61J 7/0481* (2013.01); *A61J 2200/30* (2013.01); *B65D 2203/10* (2013.01)

(58) Field of Classification Search
None
See application file for complete search history.

(56) References Cited

U.S. PATENT DOCUMENTS 5,412,372 A 5/1995 Parkhurst et al.
7,113,101 B2 9/2006 Petersen et al.
(Continued)

FOREIGN PATENT DOCUMENTS

CN 203855014 10/2014
EP 1536731 6/2005
(Continued)

*Primary Examiner* — Timothy R Waggoner
(74) *Attorney, Agent, or Firm* — Smiths IP; Lawrence Chan

(57) ABSTRACT

A blister pack for dispensing medication comprises a substantially flat backing, a plurality of blisters formed on the backing, first and second sets of conductive traces applied to the backing, a plurality of breakable resistive traces applied to the backing, and a controller adapted to detect breakage of the resistive traces under the blisters by measuring the voltage across each of either the first set of conductive traces or the second set of conductive traces. The blisters are arranged in a grid comprising rows of blisters and columns of blisters. Each of the first set of conductive traces is associated with one of the rows of blisters. Each of the second set of conductive traces is associated with one of the columns of blisters. For each blister, one or more of the resistive traces are applied to the backing under the blister to form a subcircuit, and the subcircuit connects one of the first set of conductive traces with one of the second set of conductive traces.

13 Claims, 13 Drawing Sheets

Related U.S. Application Data

(60) Provisional application No. 62/188,618, filed on Jul. 3, 2015.

(51) Int. Cl.
  B65D 75/54 (2006.01)
  B65D 75/36 (2006.01)
  *A61J 7/04* (2006.01)

(56) References Cited

U.S. PATENT DOCUMENTS

| | | | |
|---|---|---|---|
| 8,151,990 | B2 | 4/2012 | Udo et al. |
| 8,960,440 | B1 | 2/2015 | Kronberg |
| 9,622,942 | B2 * | 4/2017 | Maijala ............... B65D 75/327 |
| 2004/0189311 | A1 | 9/2004 | Glezer et al. |
| 2004/0220498 | A1 | 11/2004 | Li et al. |
| 2005/0162979 | A1 | 7/2005 | Ostergaard et al. |
| 2005/0187515 | A1 | 8/2005 | Varrichio et al. |
| 2005/0241983 | A1 * | 11/2005 | Snyder ............... G06F 19/3462 206/539 |
| 2006/0021900 | A1 | 2/2006 | Feodoroff |
| 2006/0271020 | A1 | 11/2006 | Huang et al. |
| 2007/0085690 | A1 | 3/2007 | Tran |
| 2007/0246396 | A1 | 10/2007 | Brollier |
| 2007/0273504 | A1 | 11/2007 | Tran |
| 2008/0161779 | A1 | 7/2008 | Wei |
| 2009/0194452 | A1 * | 8/2009 | Hession ............... A61J 7/0481 206/531 |
| 2010/0089791 | A1 * | 4/2010 | Rosenbaum ......... H05K 1/0286 206/531 |
| 2012/0065776 | A1 | 3/2012 | Czaja et al. |
| 2013/0023719 | A1 | 1/2013 | Bennett |
| 2013/0285681 | A1 | 10/2013 | Wilson et al. |
| 2014/0039445 | A1 | 2/2014 | Austin et al. |
| 2014/0048442 | A1 | 2/2014 | Maijala et al. |
| 2014/0239062 | A1 | 8/2014 | Nurse et al. |
| 2014/0277705 | A1 | 9/2014 | Czaja et al. |
| 2014/0294952 | A1 | 10/2014 | Anderson |
| 2014/0299504 | A1 | 10/2014 | Sena |
| 2015/0060387 | A1 | 3/2015 | Ammar |
| 2015/0068930 | A1 | 3/2015 | Alonso et al. |
| 2015/0148947 | A1 | 5/2015 | McConville et al. |
| 2015/0164741 | A1 | 6/2015 | Wilson et al. |
| 2015/0274402 | A1 | 10/2015 | Elliott |
| 2015/0286852 | A1 * | 10/2015 | Sengstaken, Jr. .. G06K 19/0716 340/10.1 |
| 2016/0008228 | A1 | 1/2016 | Forster |

FOREIGN PATENT DOCUMENTS

| | | |
|---|---|---|
| EP | 2269561 | 1/2011 |
| EP | 2704401 | 3/2014 |
| EP | 2801940 | 11/2014 |
| EP | 2844582 | 3/2015 |
| ES | 1126055 | 10/2014 |
| TW | M495849 | 2/2015 |
| WO | 2007043858 | 4/2007 |
| WO | 2009090048 | 7/2009 |
| WO | 2014145444 | 9/2014 |
| WO | 2014164833 | 10/2014 |
| WO | 2014183131 | 11/2014 |
| WO | 2015035292 | 3/2015 |
| WO | 2015048711 | 4/2015 |
| WO | 2015050438 | 4/2015 |

* cited by examiner

CONNECTED SENSOR SUBSTRATE FOR BLISTER PACKS

CROSS-REFERENCE TO RELATED APPLICATIONS

This application is a continuation-in-part of U.S. patent application Ser. No. 15/202,343 filed Jul. 5, 2016, which claims the benefit of U.S. Provisional Patent Application No. 62/188,618 filed Jul. 3, 2015, the contents of all of which are hereby incorporated by reference.

FIELD OF THE INVENTION

The present invention relates to the field of packaging and in particular, to the field of sensors for use in medication packaging.

BACKGROUND OF THE INVENTION

Blister packaging is commonly used to store medication. This type of packaging typically comprises a number of blisters formed by a thermoformed plastic that is attached to a backing made of paperboard, metallic material, or plastic. One or more pills or tablets may be stored within each of the cavities formed by the blisters. When the patient wishes to take the medication, he or she simply ruptures the portion of the backing corresponding to the appropriate blister to release the stored medication.

One example of a blister packaging for medication contains 28 cavities, arranged in 4 columns and 7 rows of cavities. Each row may correspond to a day of the week, with each column corresponding to a particular time of day (e.g. morning, afternoon, evening, bedtime, etc.). This packaging allows the patient to store a medication regimen for an entire week using a single blister pack.

In order to ensure that medication is taken in accordance with a prescribed schedule, blister packs may be provided with electronic means (e.g. circuits) for detecting when the cavities are ruptured. However, if such electronic means are bulky or cumbersome, these "smart" blister packs may face difficulties in market adoption since pharmacies may have limited shelf space. Furthermore, the cost of producing the smart blister packs should not be so high such that pharmacies and patients are discouraged from using them.

For example, United States Patent Publication No. 2015/0148947 to McConville et al. discusses a device for determining when a medication is removed from a blister pack. Each blister of the blister pack has a corresponding circuit on the backing with a different resistance associated with each circuit. When a cavity is ruptured, the corresponding circuit is broken, resulting in a reduction in the overall resistance in the device, which is detected by a controller. Although McConville et al. discusses the possibility of printing circuits directly on the backing of the blister pack, limitations in the printing process typically results in a high degree of variability in the resistances in the resulting circuits. This makes the approach in McConville et al. impractical when a large number of blisters is required, as it is very difficult to ensure that the resistances in each of the circuits will be sufficiently differently from one another to be distinguishable when a circuit is broken.

U.S. Pat. No. 8,960,440 to Kronberg also discusses a device for monitoring when cavities on a blister pack are ruptured. The device comprises a number of breakable resistive traces (each applied to the backing of a cavity) connected in parallel to each other, which is connected in series with a reference resistive trace. When a cavity is ruptured, the corresponding resistive trace is broken, resulting in a microcontroller detecting a change in the ratio of the resistance of the (parallel) breakable resistive traces with respect to the reference resistive trace. Although the device in Kronberg is able to detect that a cavity has been ruptured, it is not able to detect which particular cavity has been ruptured.

There is therefore a need for a blister pack that is both cost-effective to produce and yet capable of detecting when particular cavities are ruptured.

SUMMARY OF THE INVENTION

According to one embodiment of the invention, a blister pack for dispensing medication comprises a substantially flat backing, a plurality of blisters formed on the backing, a plurality of breakable resistive traces, a plurality of conductive traces, a power source for applying electrical power to the resistive traces and the conductive traces, and a controller. The blisters and the backing form cavities for containing the medication, and each blister is coupled with another blister to form pairs of blisters. One or more of the resistive traces are applied to the backing under each blister. For each pair of blisters, the one or more resistive traces under a first blister of the pair of blisters is connected in parallel by the conductive traces with the one or more resistive traces under a second blister of the pair of blisters. The controller detects breakage of the resistive traces under the blisters for each pair of blisters by measuring the voltage across the resistive traces under each pair of blisters.

In another embodiment, the one or more resistive traces under the first blister are connected in series. The one or more resistive traces under the second blister are connected in series.

In yet another embodiment, the one or more resistive traces under the first blister are connected in series by one or more of the conductive traces. The one or more resistive traces under the second blister are connected in series by one or more of the conductive traces.

In a further embodiment, for each pair of blisters, the one or more resistive traces under the first blister have a first total resistance and the one or more resistive traces under the second blister have a second total resistance, wherein the first total resistance is different from the second total resistance.

In yet a further embodiment, the ratio between the second total resistance and the first total resistance is between approximately 1.55 and 1.7 to 1.

In still yet a further embodiment, the ratio between the second total resistance and the first total resistance is approximately 1.6 to 1.

In another embodiment, the second total resistance is approximately 80 kΩ and the first total resistance is approximately 50 kΩ.

In still another embodiment, the blister pack further comprises a plurality of pads for connection with the controller, wherein the pads are connected to the pairs of blisters by the conductive traces.

In still yet another embodiment, each pad is connected to two pairs of blisters.

In a further embodiment, the controller is located on the backing.

In still a further embodiment, the blister pack further comprises a spine attached to the backing, wherein the pads are located on the spine and wherein the conductive traces extend from the backing onto the spine.

In yet a further embodiment, the controller is located on the spine.

In another embodiment, the resistive traces and the conductive traces are printed on the backing. The resistive traces can be printed using carbon ink. The conductive traces can be printed using conductive silver ink.

In yet another embodiment, the blister pack further comprises a controller module for housing the controller. The controller module can be adapted to transmit data comprising data on breakage of the resistive traces under the blisters.

In a further embodiment, a blister pack for dispensing medication comprises a substantially flat backing, a plurality of blisters formed on the backing, a plurality of breakable resistive traces, a plurality of conductive traces, a power source, and a controller for detecting breakage of the resistive traces under the blisters. The blisters and the backing form cavities for containing the medication. The blisters are arranged in a grid comprising columns, wherein each blister is coupled with another blister in an adjacent column to form pairs of blisters. For each blister, one or more of the resistive traces are applied to the backing under the blister to form a subcircuit. For each pair of blisters, the subcircuit under a first blister of the pair of blisters is connected in parallel by the conductive traces with the subcircuit under a second blister of the pair of blisters to form a pair of subcircuits. The conductive traces extend from the ends of each pair of subcircuits. The power source applies electrical power to the subcircuits. The controller detects breakage of the resistive traces under the blisters for each pair of subcircuits by measuring the voltage across each pair of subcircuits.

In still a further embodiment, for each pair of subcircuits, the subcircuit under the first blister has a first total resistance and the subcircuit under the second blister has a second total resistance. The first total resistance is different from the second total resistance.

In another embodiment, a substrate for application on a blister pack comprising blisters comprises a plurality of breakable resistive traces applied to the substrate, a plurality of conductive traces applied to the substrate, a power source, and a controller. For each of the blisters, one or more of the resistive traces are applied to the substrate under the blister to form a subcircuit and wherein each subcircuit is coupled with another subcircuit to form pairs of subcircuits. For each pair of subcircuits, a first subcircuit is connected in parallel by the conductive traces to a second subcircuit, wherein the conductive traces extend from the ends of each pair of subcircuits. The power source applies electrical power to the subcircuits. The controller detects breakage of the resistive traces in the subcircuits for each pair of subcircuits by measuring the voltage across each pair of subcircuits.

In yet another embodiment, the substrate further comprises an adhesive first surface for application of the substrate on the blister pack.

In still yet another embodiment, the substrate further comprises a second surface, wherein the resistive traces and the conductive traces are applied to the second surface.

In a further embodiment, a system for tracking medication use comprises a blister pack, a gateway, and a server. The blister pack comprises a substantially flat backing, a plurality of blisters formed on the backing, a plurality of breakable resistive traces, a plurality of conductive traces, a power source for applying electrical power to the resistive traces and the conductive traces, a controller, and a transmitter. The blisters and the backing form cavities for containing the medication, and each blister is coupled with another blister to form pairs of blisters. One or more of the resistive traces are applied to the backing under each blister. For each pair of blisters, the one or more resistive traces under a first blister of the pair of blisters is connected in parallel by the conductive traces with the one or more resistive traces under a second blister of the pair of blisters. The controller detects breakage of the resistive traces under the blisters for each pair of blisters by measuring the voltage across the resistive traces under each pair of blisters. The transmitter transmits data regarding breakage of the blisters. The gateway comprises a gateway receiver for receiving the data and a gateway transmitter for transmitting the data. The server comprises a server receiver for receiving the data, an analysis module to compare the data with a predetermined schedule for medication use to determine adherence with the schedule, and a communications module for sending notifications regarding the adherence with the schedule.

In another embodiment, a blister pack for dispensing medication comprises a substantially flat backing, a plurality of blisters formed on the backing, a first set of conductive traces applied to the backing, a second set of conductive traces applied to the backing, a plurality of breakable resistive traces applied to the backing, a power source configured to selectively apply electrical power to one or more of the first set of conductive traces or the second set of conductive traces, and a controller adapted to detect breakage of the resistive traces under the blisters by measuring the voltage across each of either the first set of conductive traces or the second set of conductive traces. The blisters and the backing form cavities for containing the medication, and the blisters are arranged in a grid comprising rows of blisters and columns of blisters. Each of the first set of conductive traces is associated with one of the rows of blisters such that all of the blisters for each row of associated blisters is connected. Each of the second set of conductive traces is associated with one of the columns of blisters such that all of the blisters for each column of associated blisters is connected. For each blister, one or more of the resistive traces are applied to the backing under the blister to form a subcircuit, and the subcircuit connects one of the first set of conductive traces with one of the second set of conductive traces.

In still a further embodiment, each of the subcircuits has a total resistance, and the total resistance for each of the subcircuits is substantially identical to one other.

In yet still a further embodiment, the total resistance is approximately 10 kΩ.

In yet another embodiment, the blister pack further comprises a selector adapted to selectively choose one of the first set of conductive traces to input to the controller.

In still yet another embodiment, the controller is further adapted to determine iteratively whether resistive traces under each of the blisters have been broken.

In a further embodiment, a blister pack for dispensing medication comprises a substantially flat backing, a controller, a plurality of blisters formed on the backing, a plurality of breakable resistive traces applied to the backing, and a plurality of conductive traces applied to the backing. The blisters and the backing form cavities for containing the medication, and wherein each of the blisters is generally defined by two opposed long edges and two opposed short edges. For each blister, one or more of the resistive traces are applied to the backing under the blister to form a subcircuit, and the one or more of the resistive traces cross each of the long edges and each of the short edges at least once. The conductive traces connect the subcircuits to the controller. The controller is adapted to detect breakage of the resistive traces under the blisters by measuring the voltage across the subcircuits.

In yet a further embodiment, the one or more of the resistive traces cross each of the long edges at least twice and each of the short edges at least once.

In another embodiment, a blister pack for dispensing medication comprises a substantially flat backing, a controller, a plurality of blisters formed on the backing, a plurality of breakable resistive traces applied to the backing, and a plurality of conductive traces applied to the backing. The blisters and the backing form cavities for containing the medication. For each blister, at least two of the resistive traces are applied to the backing under the blister to form a subcircuit, and the resistive traces in the subcircuit are connected in parallel. The conductive traces connect the subcircuits to the controller. The controller is adapted to detect breakage of the resistive traces under the blisters by measuring the voltage across the subcircuits.

In still yet a further embodiment, the subcircuit comprises at least three resistive traces connected in parallel.

In another embodiment, each of the blisters is generally defined by two opposed long edges and two opposed short edges, and for each blister, the resistive traces cross each of the long edges at least twice and each of the short edges at least once.

In yet another embodiment, the backing comprises a plurality of perforation perimeters proximate to the perimeters of the blisters. The perforation perimeters each comprise alternating perforations and unperforated gaps. A first width of the unperforated gap is approximately 1.5 millimeters proximate to where the resistive traces cross either the long edges or the short edges, and a second width of the unperforated gap is approximately 0.3 millimeters elsewhere.

The foregoing was intended as a summary only and of only some of the aspects of the invention. It was not intended to define the limits or requirements of the invention. Other aspects of the invention will be appreciated by reference to the detailed description of the preferred embodiments. Moreover, this summary should be read as though the claims were incorporated herein for completeness.

BRIEF DESCRIPTION OF THE DRAWINGS

The invention will be described by reference to the drawings thereof, in which.

DETAILED DESCRIPTION

Figure 1:
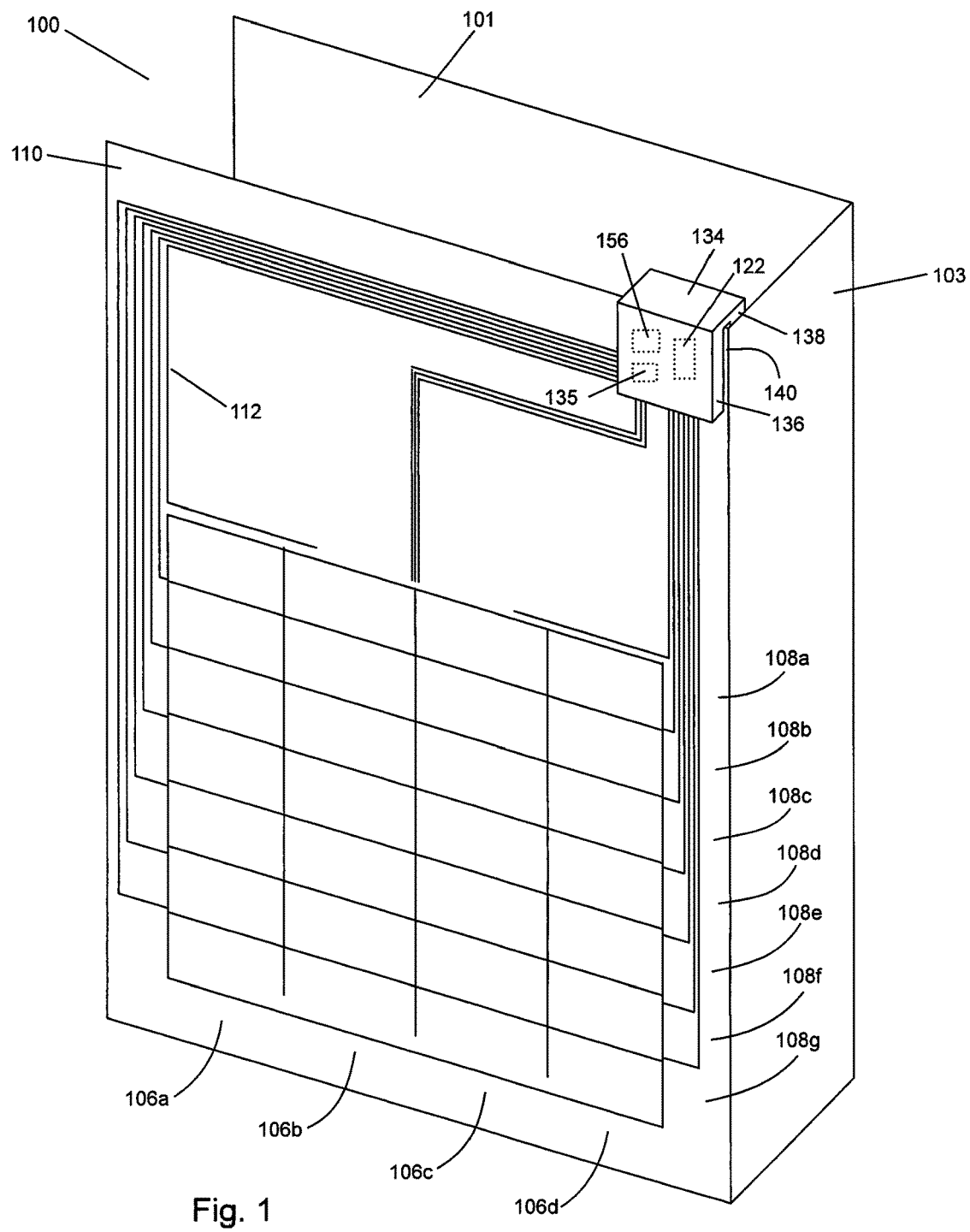
FIG. 1 shows a blister pack generally illustrating the invention.
Figure 2:
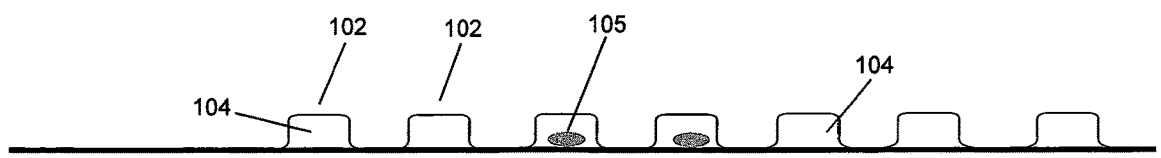
FIG. 2 is a side view of the backing of the blister pack according to the invention.

Referring to FIGS. 1 and 2, a blister pack 100 in accordance with an embodiment of the present invention comprises one or more blisters 102, each of which defines a cavity 104 for holding medication 105 (e.g. tablets, capsules, etc.). The blisters 102 may be formed by a thermoformed plastic or any other suitable material. In the embodiments shown in the figures, the blister pack 100 comprises twenty-eight blisters 102, arranged generally in a grid of four columns 106 (i.e. columns 106a-106d) and seven rows 108 (i.e. rows 108a-108g). In this embodiment, each of the rows 108 may represent one day of a week, with each of the columns 106 representing a particular time in the day for taking medication. However, it is understood that other numbers of blisters 102 and other arrangements of blisters 102 may also be used.

The blister pack 100 can also comprise a cover 101 and a spine 103. The cover 101 and spine 103 provides a covering for the blister pack 100 to hide the blisters 102 from view.

Figure 3:
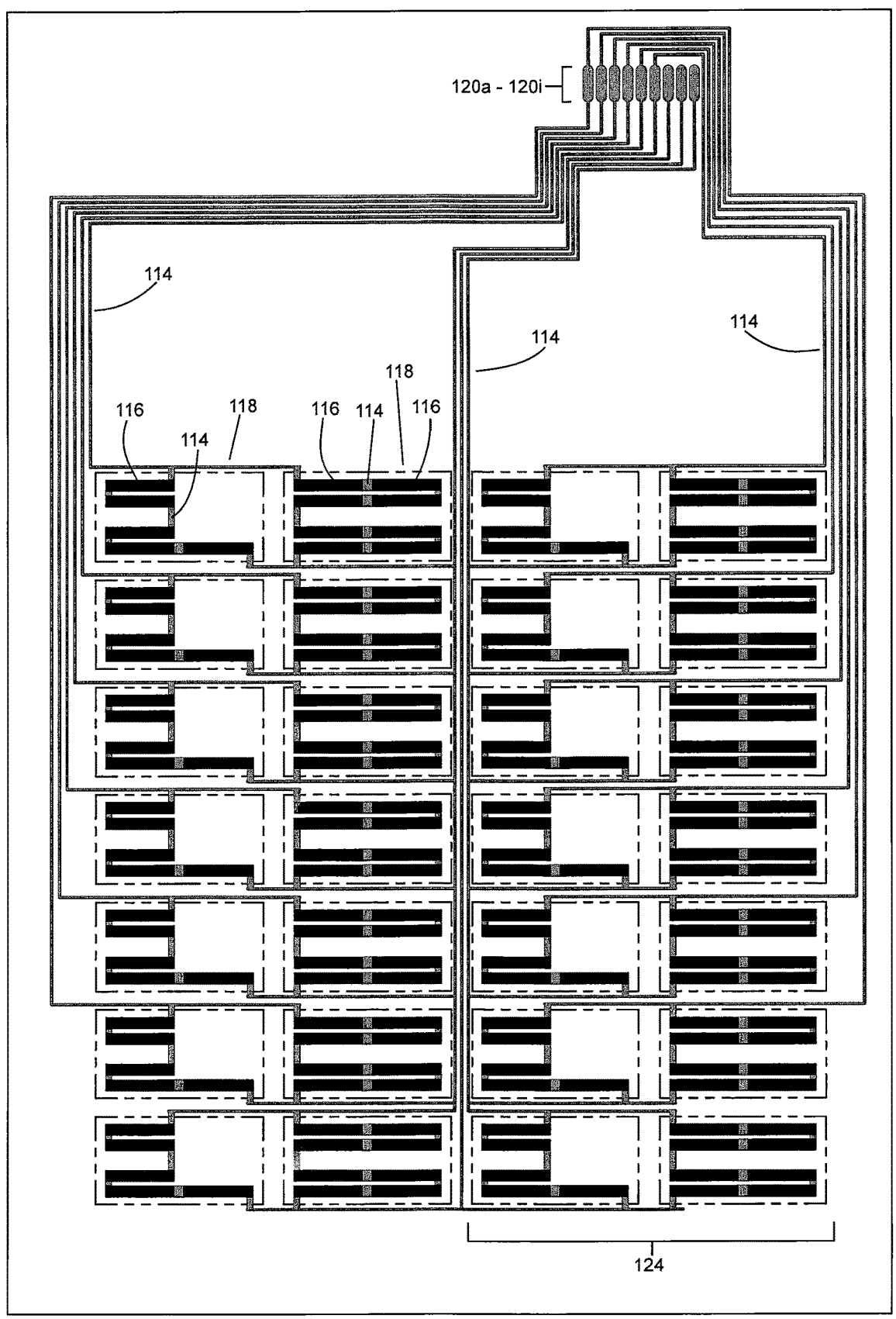
FIG. 3 shows a blister pack illustrating an embodiment of the invention.

The blisters 102 are attached to a backing 110. The backing 110 is preferably flat and can be generally made from paperboard, plastic, or any other suitable material. The backing 110 comprises a plurality of traces 112, which preferably include both conductive traces 114 (shown in gray lines) and breakable resistive traces 116 (shown in thick black lines). FIG. 3 shows an arrangement of the traces 112 in accordance with an embodiment of the invention. In this embodiment, each of the blisters 102 is associated with one or more resistive traces 116, with each of the blisters 102 preferably located directly on top of its associated one or more resistive traces 116 (the location of the blisters 102 are generally indicated in dotted line). Preferably, the traces 112 are located on the side of the backing 110 opposite the blisters 102; however, it is also contemplated that the traces 112 may be on the same side of the backing 110 as the blisters 102.

The traces 112 are preferably printed on the backing 110. For example, conductive traces 114 may be printed using highly conductive silver ink, while resistive traces 116 may be printed using carbon ink. Other methods and techniques for forming the traces 112 may also be used. For example, the traces 112 may be stamped onto the backing 110 using aluminum, copper, and/or other conductive materials.

Referring again to FIG. 3, where the blister 102 is associated with one or more resistive traces 116, those resistive traces 116 are preferably connected together in series by one or more conductive traces 114. However, the resistive traces 116 can also be directly connected together in series. For example, the blister 102 located in column 106a and row 108a is associated with five resistive traces 116 connected in series by four conductive traces 114. The adjacent blister 102 located in column 106b and row 108a is associated with eight resistive traces 116 connected in series by seven conductive traces 114. Other numbers and combinations of resistive traces 116 and conductive traces 114 are also possible.

The resistive traces 116 associated with each of the blisters 102 (along with the conductive traces 114 connecting such resistive traces 116) form subcircuits 118, with each blister 102 being associated with one such subcircuit 118. As the resistive traces 116 in each subcircuit 118 are connected in series, each subcircuit 118 has an effective resistance R that is equal to the sum of the individual resistances of the resistive traces 116.

The resistive traces 116 in each subcircuit 118 are preferably arranged in a serpentine, winding, or otherwise extended manner in order to reliably ensure that when the portion of the backing 110 behind a particular blister 102 is ruptured, the associated subcircuit 118 is broken.

Figure 4:
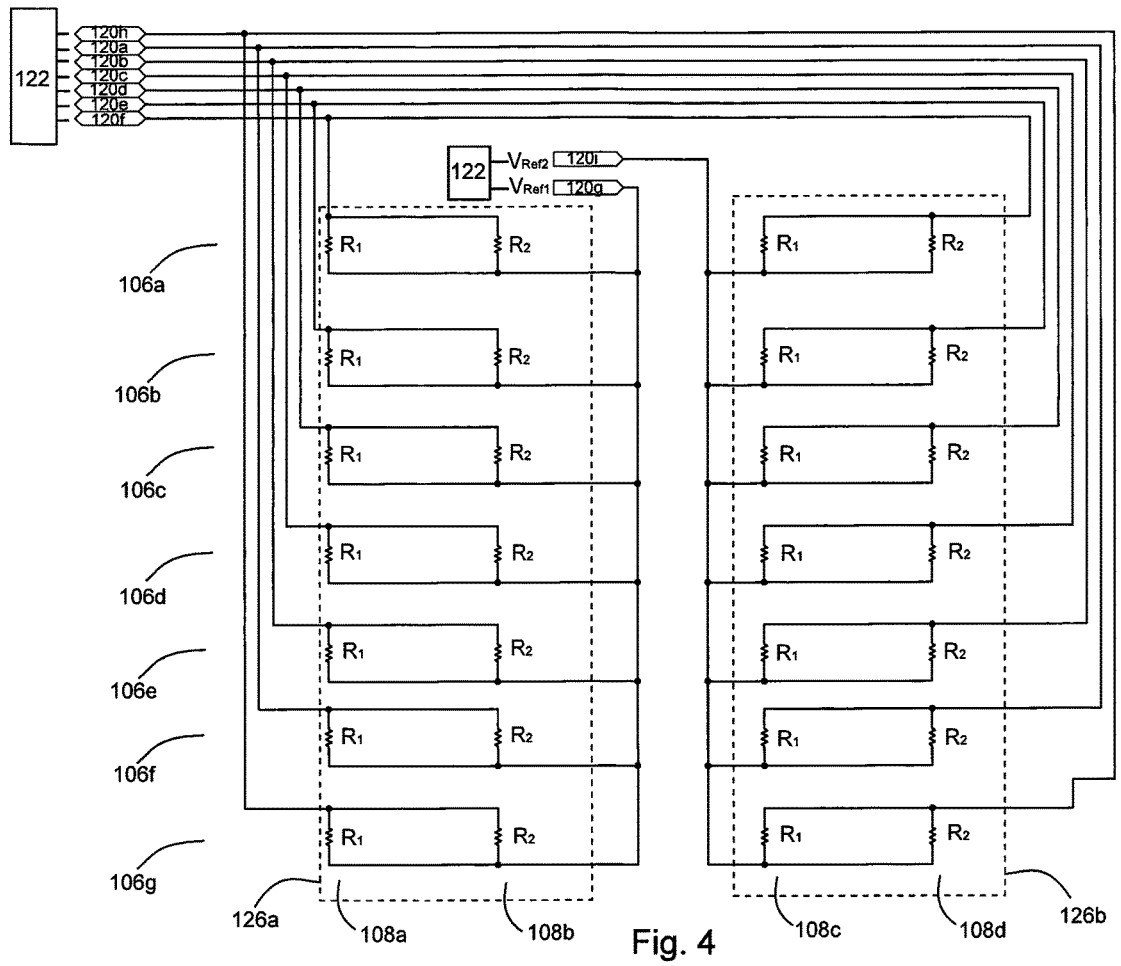
FIG. 4 shows a schematic diagram illustrating the embodiment of the invention of FIG. 3.

Referring again to FIG. 3, the various subcircuits 118 are connected by conductive traces 114 to pads 120, which can then receive a controller 122. In the embodiment shown in FIG. 3, there are nine pads 120 (i.e. pads 120a-120i). FIG. 4 shows a schematic representation of the connections between the subcircuits 118. Each subcircuit 118 is connected in parallel with an adjacent subcircuit 118. For example, each of the subcircuits 118 in column 106a is connected in parallel with their adjacent subcircuit 118 in column 106b. Similarly, each of the subcircuits 118 in column 106c is connected in parallel with their adjacent subcircuit 118 in column 106d. In this manner, the twenty-eight subcircuits 118 are divided into fourteen pairs 124 of subcircuits 118.

The fourteen pairs 124 can be divided into two zones 126 (i.e. zones 126a, 126b). In the embodiment shown in FIGS. 3 and 4, zone 126a comprise the subcircuits 118 in the rows 108a and 108b, while zone 126b comprise the subcircuits 118 in the rows 108c and 108d. However, other ways of dividing the subcircuits 118 are also possible.

A first end 128 of each of the pairs 124 in a particular zone 126 is electrically connected together in common by conductive traces 114 to one of the pads 120, with each zone 126 being connected to a different one of the pads 120. For example, in the embodiment shown in FIGS. 3 and 4, all of the pairs 124 in zone 126a are connected on their first ends 128 to pad 120g, while all of the pairs 124 in zone 126b are connected on their first ends 128 to pad 120i. Voltage may be applied to those pads 120 to which the first ends 128 are connected (represented as $V_{ref1}$, $V_{ref2}$ in FIG. 4).

A second end 130 of each of the pairs 124 is also electrically connected by conductive traces 114 to the pads 120. In particular, the second ends 130 of each pair 124 in a particular zone 126 are each connected to different pads 120. However, the second ends 130 of each pair 124 in a particular zone 126 are also electrically connected to the second ends 130 of another pair 124 in another zone 126. For example, in the embodiment shown in FIGS. 3 and 4, the second ends 130 of both pairs 124 in row 108a are electrically connected together (at pad 120f). Similarly, the second ends 130 of both pairs 124 in row 108b are electrically connected together (at pad 120e). Both pairs 124 in row 108c are electrically connected together at pad 120d. Both pairs 124 in row 108d are electrically connected together at pad 120c. Both pairs 124 in row 108e are electrically connected together at pad 120b. Both pairs 124 in row 108f are electrically connected together at pad 120a. Finally, both pairs 124 in row 108g are electrically connected together at pad 120h. Other arrangements for connecting pairs 124 from two different zones 126 are also possible.

Figure 5:
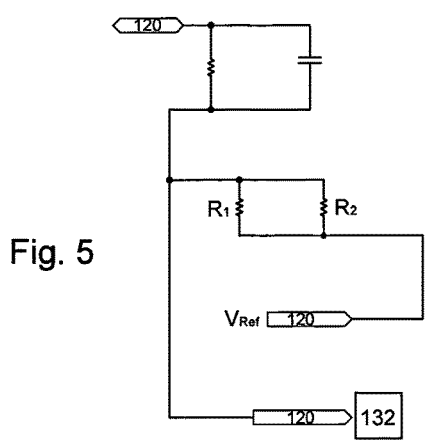
FIG. 5 shows a schematic diagram illustrating an equivalent circuit for a portion of the schematic diagram shown in FIG. 4.

FIG. 5 is a schematic representation of the equivalent circuit for a particular pair 124. The two subcircuits 118 (each having an effective resistance R) are connected in parallel. The first end 128 for the pair 124 is electrically connected to pad 120 to which voltage may be applied. The second end 130 is electrically connected to another pad 120.

As described above, each of the subcircuits 118 has an effective resistance R. For any particular pair 124, the two subcircuits 118 in that pair 124 would have effective resistances of $R_1$ and $R_2$, respectively. Since the two subcircuits 118 in each pair 124 are connected in parallel, the total effective resistance $R_T$ for the pair 124 would be as follows:

$$R_T = \frac{R_1 R_2}{R_1 + R_2}$$

If one of the subcircuits 118 in the pair 124 was broken (i.e. the portion of the backing 110 for the blister 102 corresponding to that subcircuit 118 is broken), then the total effective resistance $R_T$ for the pair will change. For example, if the subcircuit 118 corresponding to $R_1$ was broken, then the total effective resistance $R_T$ will simply be equal to $R_2$. Similarly, if the subcircuit 118 corresponding to $R_2$ was broken, then the total effective resistance $R_T$ will be equal to $R_1$. If both subcircuits 118 in the pair 124 were broken, then this would result in an open circuit.

Accordingly, the overall resistive characteristics of the pair 124 will depend on whether neither, one, or both of the subcircuits 118 in the pair 124 are broken. This can be determined, for example, by monitoring the voltage drop across the pair 124.

In order to distinguish between the two subcircuits 118 when only one of them is broken, it is necessary that the respective effective resistances $R_1$, $R_2$ of the two subcircuits 118 be different from one another. Because of current limitations in printing technology, a variance of up to ±20% in the actual resistance of printed traces 112 is possible (compared to the expected resistance). However, if the difference between the resistances is too great (e.g.

$R_1 \gg R_2$), then it may be difficult to discern the change in voltage drop when one of the subcircuits 118 (e.g. when $R_1$ is broken).

In view of this, it has been found that the ratio of $R_2$ to $R_1$ should be preferably between approximately 1.55 and 1.7, and more preferably, approximately 1.6. For example, in the embodiment shown in FIGS. 3 and 4, the resistances used for $R_1$ and $R_2$ are approximately 50 kΩ and 80 kΩ respectively, giving a ratio for $R_2/R_1$ of approximately 1.6. In the embodiment shown in FIG. 3, each of the resistive traces 116 have a resistance of approximately 10 kΩ. As a result, all of the subcircuits 118 in columns 106a and 106c have effective resistances of approximately 50 kΩ (i.e. five resistive traces 116), while all of the subcircuits 118 in columns 106b and 106d have effective resistances of approximately 80 kΩ (i.e. eight resistive traces 116). However, it is important to note that the actual resistances used by the various subcircuits 118 are not as important as the relative ratio of the resistances of the two subcircuits 118 in each pair.

Although the embodiment in FIG. 3 shows two subcircuits 118 connected in parallel to form pairs 124, it is understood that it is also possible to connect three or more subcircuits 118 in parallel to form larger groupings. One limitation is the relatively large variance in the actual resistance of printed traces 112 (i.e. up to ±20%); however, with improved accuracy, it is possible to use three or more subcircuits 118 in a grouping and still differentiate as to when a particular subcircuit 118 is broken.

In addition, although the embodiment in FIG. 3 shows each subcircuit 118 connected in parallel with a vertically adjacent subcircuit 118 (in an adjacent column 106), it is understood that horizontally adjacent subcircuits 118 may be connected together instead. Depending on the number of columns 106 and rows 108 in the blister pack 100, the precise arrangement and interconnections of the subcircuits 118 may vary in order to reduce the number and length of the traces 112, and to evenly spread the traces 112 between columns 106.

The operation of the blister pack 100 will now be described. The controller 122 may periodically apply voltage at pads 120g or 120i. In particular, when the blisters 102 in zone 126a are to be checked to determine if any of the respective cavities 104 have been ruptured, voltage is applied to pad 120g. When the blisters 102 in zone 126b are to be checked, voltage is applied to pad 120i. In the example where voltage is applied to pad 120g (i.e. to check the blisters 102 in zone 126a), the controller 122 can determine the voltage drop across each of the pairs 124 spanning the columns 106a and 106b. This is done through pads 120a, 120b, 120c, 120d, 120e, 120f, and 120h. The controller 122 may use an analog-to-digital converter (ADC) 132 to process this data and from this, the controller 122 can determine whether neither, one, or both of the blisters 102 in each pair 124 of zone 126a have been broken. This data can then be stored by the controller 122.

For each pair 124, there are four possible combinations: (1) both subcircuits 118 are intact; (2) the first of the subcircuits 118 is broken but the second of the subcircuits 118 is intact; (3) the first of the subcircuits 118 is intact but the second of the subcircuits 118 is broken; and (4) both subcircuits 118 are broken. Because the resistances of each of the two subcircuits 118 are different from one another (and preferably in the ratio of between approximately 1.55 and 1.7), each of the four combinations will result in discernible differences, either in the total effective resistance (in cases (1) to (3)) or in an open circuit (in case (4)). This can be done for each of the pairs 124 in zone 126a.

After the results in zone 126a have been determined, the condition of the blisters 102 in zone 126b can be determined by the controller 122 applying voltage to pad 120i. In a similar manner to that of zone 126a, the condition of the blisters 102 in each of the pairs 124 in zone 126b can be determined.

Consequently, by selectively applying voltage to either pads 120g or 120i, the condition of each of the blisters 102 on the blister pack 100 can be determined. This data can be stored on the controller 122 for further processing or transmittal.

By having the second ends 130 of the two pairs 124 in each row 108 share a common pad 120, it is possible to reduce the number of pads 120 required to nine. This allows the use of a smaller controller 122, resulting in a lower cost.

One potential issue with the embodiment shown in FIG. 3 is the presence of stray or "ghost" current that may interfere with the readings by the controller 122. This ghost current is the result of residual current travelling through the various subcircuits 118. In order to counteract this, when the voltage drop for a particular pair 124 in a row 108 is being determined by the controller 122, the other rows 108 would be set to "LOW" (or ground). This can be done through the controller 122 (through the pads 120). Alternatively, a digital-to-analog converter (DAC) may be used to provide an additional current in the circuit to cancel the ghost current.

The traces 112 can be created by a two-step process of first printing the conductive traces 114 and then printing the resistive traces 116.

Figure 6:
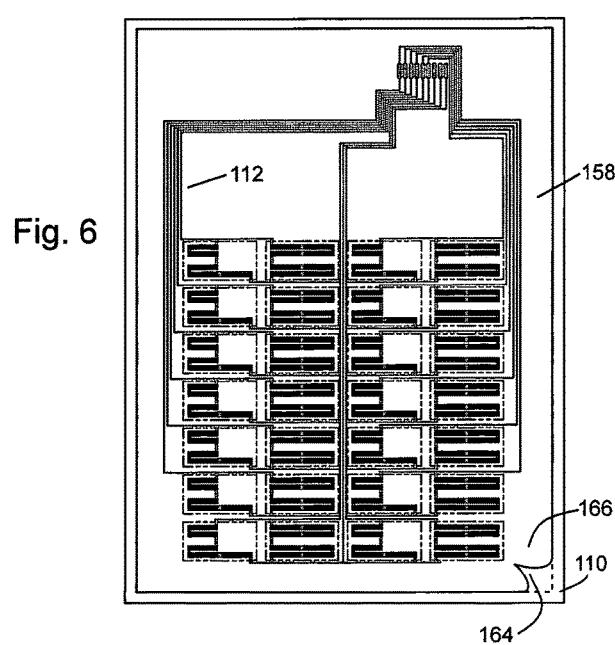
FIG. 6 shows another embodiment of the invention where a substrate according to the invention is attached to the backing of a blister pack.

Referring to FIG. 6, instead of applying the traces 112 directly to the backing 110 of the blister pack 100 (e.g. by printing, etc.), the traces 112 may be first applied to an intermediate substrate 158, which is then applied to the backing 110 of the blister pack 100. For example, the intermediate substrate 158 can have an adhesive first surface 164 for application onto a conventional blister pack. In this manner, conventional blister packs can be converted into "smart" blister packs. The traces 112 can be applied to a second surface 166 of the intermediate substrate 158.

In addition, the backing 110 or the intermediate substrate 158 can be implemented using only one sheet of material, with graphics printed on one side and the traces 112 applied (e.g. printed) to the other side. As such, the backing 110 or the intermediate substrate 158 requires minimal layers, making it easier to punch through to the cavities 104.

Referring to FIG. 1, the controller 122 may be housed within a controller module 134. The controller module 134 may also comprise a power source 156, such as a battery. In one embodiment, the controller module 134 comprises first and second portions 136, 138 defining a slot 140 for receiving a portion of one end of the backing 110. In the embodiment shown in FIG. 1, the shape of the controller module 134 is generally rectangular; however, it is understood that any shapes may be possible. The controller module 134 allows for the easy attachment to and detachment from the blister pack 100. The pads 120 make contact with the inner wall of the first portion 136. The slot 140 is preferably of such thickness to allow for snug attachment of the controller module 134 to the backing 110. In the embodiment shown in FIG. 1, the pads 120 and the controller module 134 are located such that the controller module 134 lies flush with the spine 103. This allows for the controller module 134 to be easily attached to and detached from the backing 110 without fear that the controller module 134 may be misaligned with the pads 120. Alternatively, guides can be printed on the backing 110 to allow for the alignment of the controller module 134 with the pads 120. In addition, physical guides (e.g. made of plastic, paperboard, etc.) can be provided to assist in aligning the controller module 134 with the pads 120.

Referring again to FIGS. 1 and 2, the pads 120 are preferably located on the backing 110 (or if the intermediate substrate 158 is used, on the intermediate substrate 158), with the controller module 134 directly connected to the pads 120 via a sliding or snap-on connection, such as spring pins. In this embodiment, the pins on the controller module 134 make direct electrical contact with the pads 120.

Figure 7:
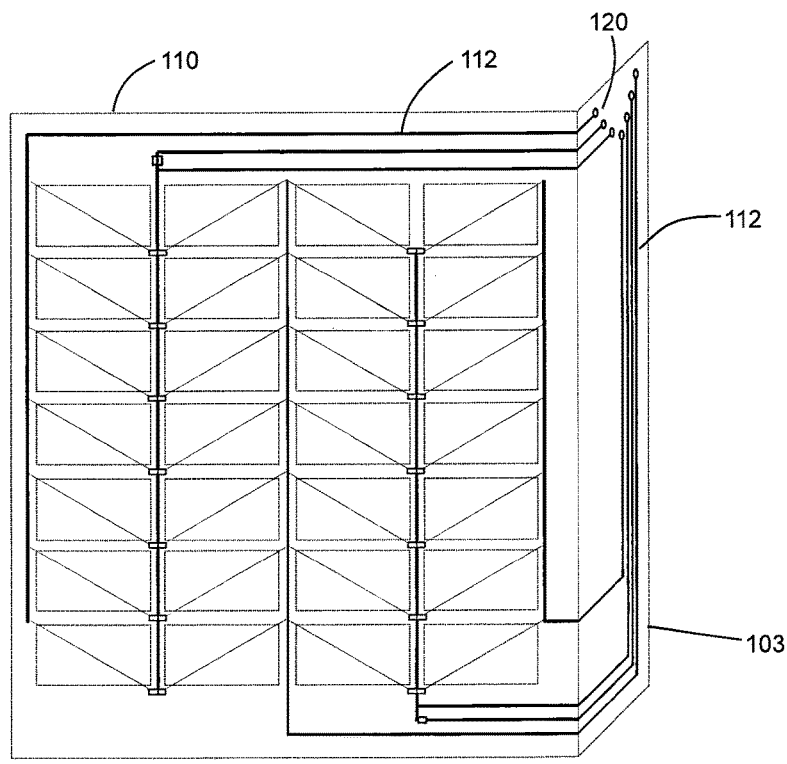
FIG. 7. shows another embodiment of the invention with the traces extending onto the spine.
Figure 8:
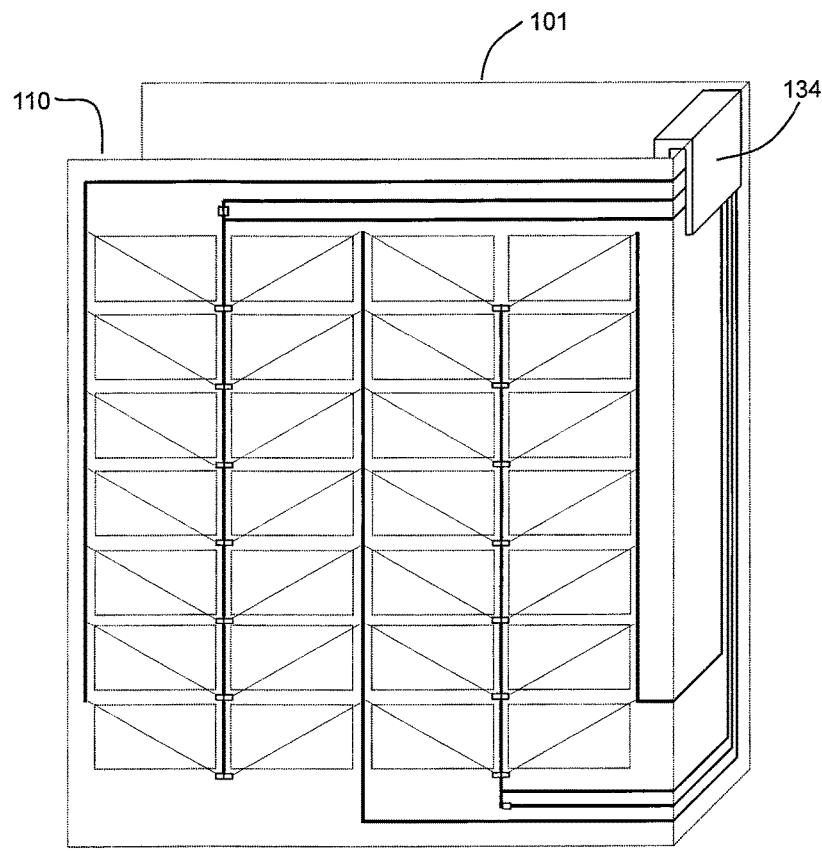
FIG. 8 shows another embodiment of the invention with the controller module attached to the spine.

In another embodiment, the tight space requirements of the blister pack 100 may not leave room for the controller module 134 on the backing 110. In this embodiment, the controller module 134 can instead be located on the spine 103, as shown in FIGS. 7 and 8. The traces 112 extend across the edge of the backing 110 and onto the spine 134, with the pads 120 being located on the spine 134.

Figure 9:
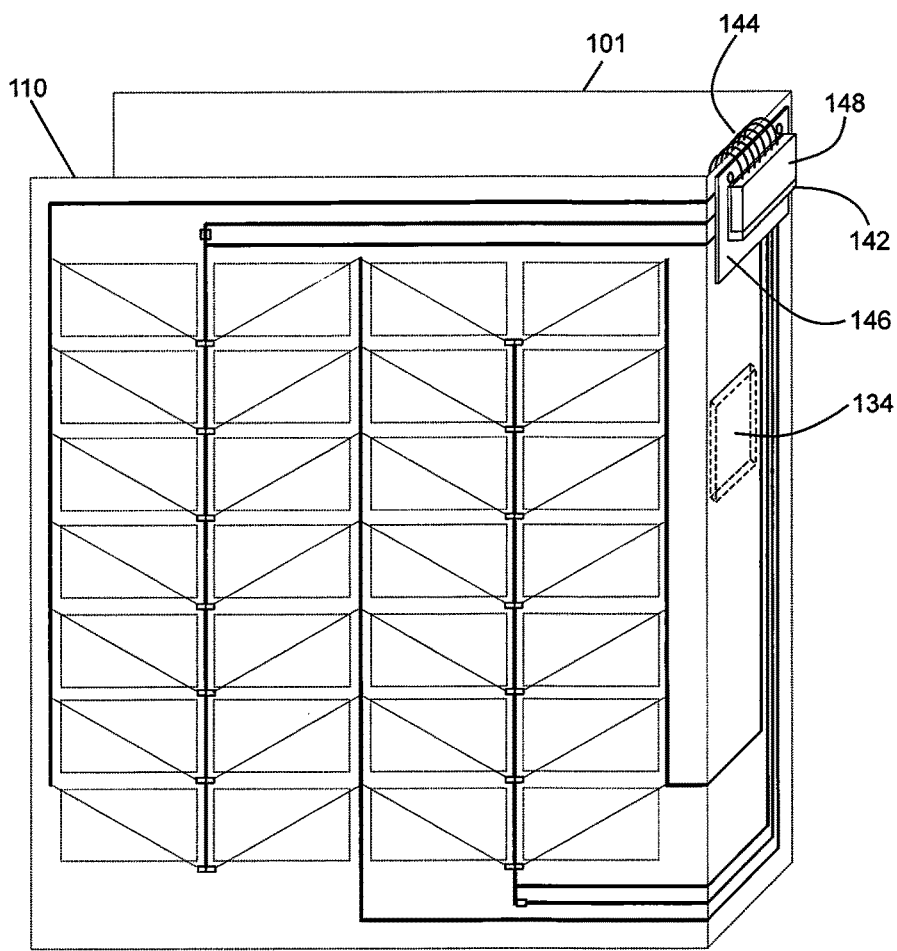
FIG. 9 shows another embodiment of the invention with the controller module located within the blister pack.

In another embodiment, the controller module 134 may be located within the blister pack 100 (e.g. within a pocket inside the blister pack 100). The controller module 134 can be attached to the blister pack 100 via an intermediary connector 142, which itself can be attached to the pads 120. In the embodiment shown in FIG. 9, the pads 120 are located on the spine 134. The intermediary connector 142 is electrically connected to the controller module 134 using one or more wires 144. Alternatively, instead of one or more wires 144, a bus wire 146 may also be used to connect the intermediary connector 142 with the controller module 134.

Figure 10A:
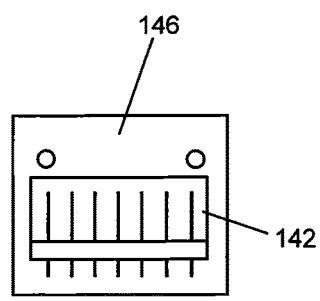
FIGS. 10a and 10b are top and bottom views, respectively, of the breakout board shown in FIG. 9.
Figure 10B:
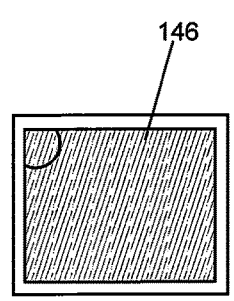
Figure 11A:
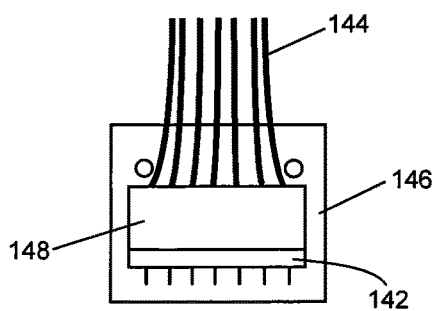
FIGS. 11a and 11b are top and bottom views, respectively, of the breakout board of FIGS. 10a and 10b with the intermediary connector attached.
Figure 11B:
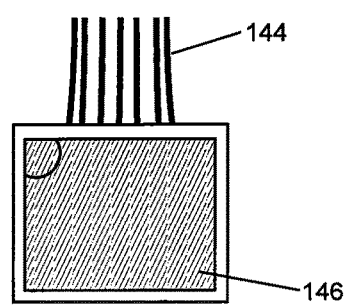

Referring to FIGS. 10*a* and 10*b*, the intermediary connector 142 can be attached to the pads 120 in a number of ways. For example, the intermediary connector 142 can sit on a breakout board 146 that is itself placed over and in electrical contact with the pads 120. The breakout board 146 can be securely attached to the spine 134 using glue, conductive tape, or some other form of adhesive. Once the intermediary connector 142 has been attached to the pads 120, the controller module 134 can be plugged into the intermediary connector 142 using a connector plug 148, as shown in FIGS. 11*a* and 11*b*.

Figure 12:
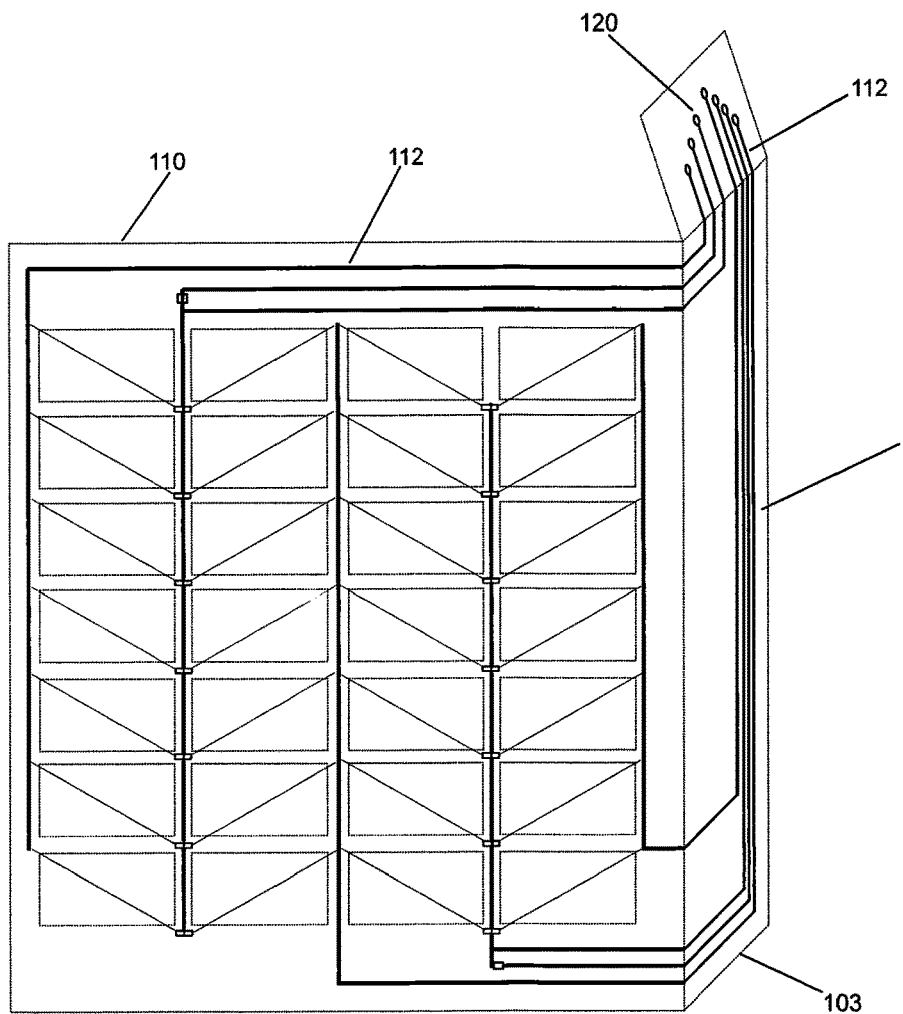
FIG. 12 shows another embodiment of the invention with the traces extending onto the spine and flap.
Figures 13A, 13B:
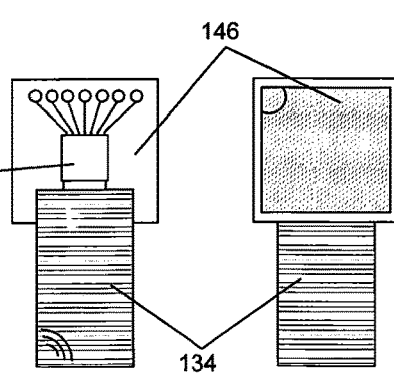
FIGS. 13a and 13b are top and bottom views, respectively, of an alternative embodiment of the breakout board.
Figures 14A, 14B, 14C:
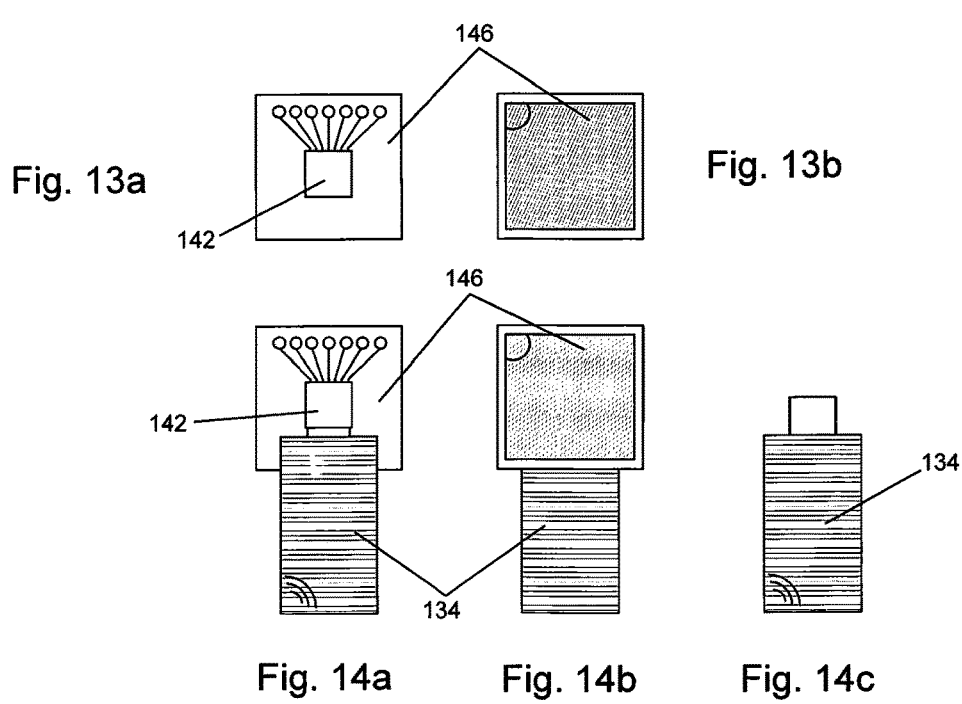
FIGS. 14a and 14b are top and bottom views, respectively, of the breakout board of FIGS. 13a and 13b with the controller module attached.
FIG. 14c is a top view of the controller module of FIGS. 13a and 13b.

In another embodiment, the blister pack 100 may further comprise a flap 150 extending from either the backing 110 or the spine 126. The traces 112 extend across flap 150, with the pads 120 being located on the flap 150. For example, in the embodiment shown in FIG. 12, the flap 150 extends from the spine 126, with the traces 112 extending across both the spine 126 and the flap 150. In this manner, the pads 120 can be hidden with the blister pack 100 (i.e. the flap 150 can be folded down between the spine 126 and the backing 110). With this embodiment, the intermediary connector 142 is not necessary.

FIGS. 13*a*, 13*b*, 14*a*, and 14*b* shows another embodiment in which the controller module 134 and the intermediary connector 142 can both reside on the breakout board 146.

The controller module 134 can be connected into the intermediary connector 142 in a number of ways. Ideally, this connection type is selected to enable a snug connection and to provide the ability to keep the connection without the need for additional points of contact between the controller module 134 and the blister pack 100. The use of an inexpensive connection type will promote the disposable nature of the blister pack 100. Furthermore, the ability to easily attach and detach the controller module 134 can allow for separation of the blister packs 100 from the controller modules 134 during storage and transportation, with assembly required only before dispensing medication. The blister packs 100 can themselves be stacked for minimum space occupancy. This allows for the blister packs 100 to be used by automated robotic blister pack dispensing equipment, such as those manufactured by Synmed.

Figure 15:
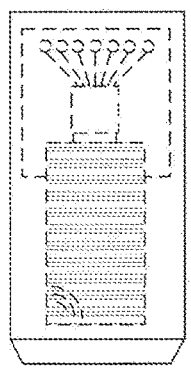
FIG. 15 is a top view of a compartment for holding the controller module.

Referring to FIG. 15, the intermediary connector 142 and the controller module 134 can be hidden inside a compartment 154 within the blister pack 100. The compartment 154 may be made from the same material as the backing 110 (e.g. paperboard, etc.). This allows the intermediary connector 142 and the controller module 134 to be protected from damage and hidden from view. When the blister packs 100 are dispensed, the compartment 154 can be opened to allow for the insertion of the controller module 134 and the intermediary connector 142.

Figure 16:
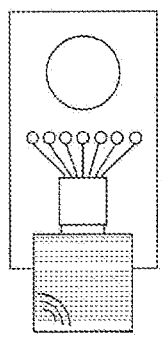
FIG. 16 is a top view of an embodiment of a controller module with a power source.

In another embodiment (shown in FIG. 16), the size of the controller module 134 can be reduced by moving the power source 156 from the controller module 134. Instead, the power source 156 may be located on the backing 110 or on the breakout board 146. The power source 156 is only needed to remain operative for a limited, defined period of time (e.g. from the moment of the dispensing of the blister pack 100 to the day by which the contents of the blister pack 100 are expected to be used up, plus some additional margin). For example, if the blister pack 100 organizes medications for a week, and four blister packs 100 are dispensed for a month, the capacity of the power source 156 can be selected such as to allow all four blister packs 100 to be operative for a little over a month, but not much longer. The power source 156 can comprise conventional batteries, printable batteries, super capacitors, and the like.

Alternatively, the controller module 134 can also be disposable (rather than reusable). In such an embodiment, the controller module 134 can either reside on its own board or be located directly on the blister pack 100. Various techniques for accommodating the controller module 134 directly on the blister pack 100 can be used, including using manufactured or printed components, various adhesives, etc.

Various techniques can also be used in optimizing the determination of when certain blisters 102 are broken. For example, as blisters 102 are broken, the events are recorded. Later, if there is an ambiguous reading pointing to two or more possible breakages of another blister 102, the controller 122 may be able to resolve this by assuming that the same blisters 102 cannot be broken more than once. By tracking a list of broken blisters 102, it may be possible to use elimination to exclude unexpected combinations. Similarly, if blisters 102 are expected to be broken within a particular time frame and there is aliasing showing alternative combinations of blisters 102 that are supposed to be broken at other times, the controller 122 can assume the most likely combination. This can be confirmed by the controller 122 in the future once more blisters 102 are broken. In addition, the controller 122 can implement de-bouncing techniques to check readings multiple times over a period of time before confirming.

Furthermore, in addition to detecting the breakage of the blisters 102, the controller 122 can also process data, such as, for example, process data for communicating the status of the blisters 102 either locally or to a remote service (e.g. through the Internet). This data can then be used and further processed to generate reminders or notifications to patients.

In addition, the controller 122 can implement techniques to extend the life of the power source 156. For example, if multiple weekly blister packs 100 are dispensed over the course of a month, only one blister pack 100 is likely to be used at a time. One way to minimize the draw of power from the power source 156 is the keep the blister packs 100 in "deep sleep" until a certain event is triggered (e.g. the breaking of a blister 102, the picking up of a blister pack 100, etc.). Alternatively, this can be done by utilizing a time driven interrupt, which can be a preprogrammed wakeup value (e.g. once or several times a day or once every several days). If the controller 122 detects the triggering event or the interrupt, the frequency of wakeups can increase, thereby resulting in the blister pack 100 being read more often. The controller 122 can also throttle (e.g. decrease) the frequency of wakeups at night or immediately after the breakage of a blister 102 or at other times when detection is unnecessary.

Figure 17:
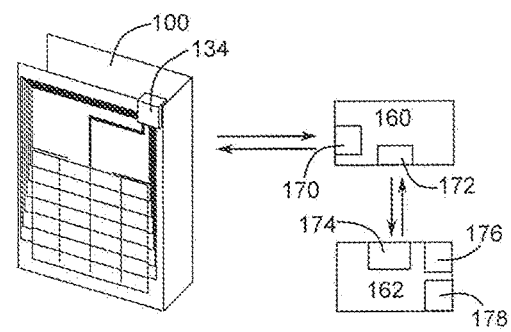
FIG. 17 shows the communications among the blister pack, gateway, and server.

The controller module 134 preferably has wireless functionality for transmitting data via the Internet. For example, the controller module 134 can comprise a radio or transmitter 135 for short-range low-power radio interfaces, such as ZigBee, Z-Wave, BLE or its variants, AM/FM, or RF over an open frequency band. Referring to FIG. 17, the controller module 134 can connect to a gateway 160 using one or more of these short-range radio interfaces. The gateway 160 comprises a gateway receiver 170 for receiving data from the radio 135 and a gateway transmitter 172 for transmitting data. The gateway 160 can serve as a bridge between such short-range radio interfaces and the Internet, using protocols such as LTE/GPRS/CDMA or other cellular standards, Wi-Fi, Ethernet, or a combination thereof. The gateway 160 can run from batteries or some other power supply. The data from the controller module 134 may be transmitted to the gateway 160 in real-time for immediate notification or analysis. Alternatively, the data may be stored by the controller module 134 for later transmittal. In case of network failure, the gateway 160 can preferably continue to store captured data until the network connection is restored.

For example, the gateway 160 may transfer data (e.g. over the Internet, in real-time or in batch) to a central server 162, which can then analyze the data to determine whether the blisters 102 are being broken (and implicitly, whether medication is being taken) in accordance with a predetermined schedule. The server 162 comprises a server receiver 174 for receiving data from the gateway transmitter 172. The server 162 preferably comprises an analysis module 176 for determining whether the blisters 102 are being broken in accordance with the schedule. Notifications or reminders may be sent by the server 162 through a communications module 178 if, for example, there are deviations from the schedule. The notifications or reminders can be sent by the server 162 to the gateway 160 and then from the gateway 160 to the controller module 134. Such notifications or reminders can be sent immediately so that corrective action can be taken as soon as possible.

The need for the gateway 160 comes from the desirability to make the controller modules 134 inexpensive. However, if the price of long-range low-power wireless radios is sufficiently low, the controller module 134 can incorporate such radios for communication directly with the Internet. Examples of such long-range radios include LTE Cat-M1, NB-IoT, EC-EGPRS, eDRX, the latest Wi-Fi, SigFox, LoRa, and other similar technologies.

Figure 18:
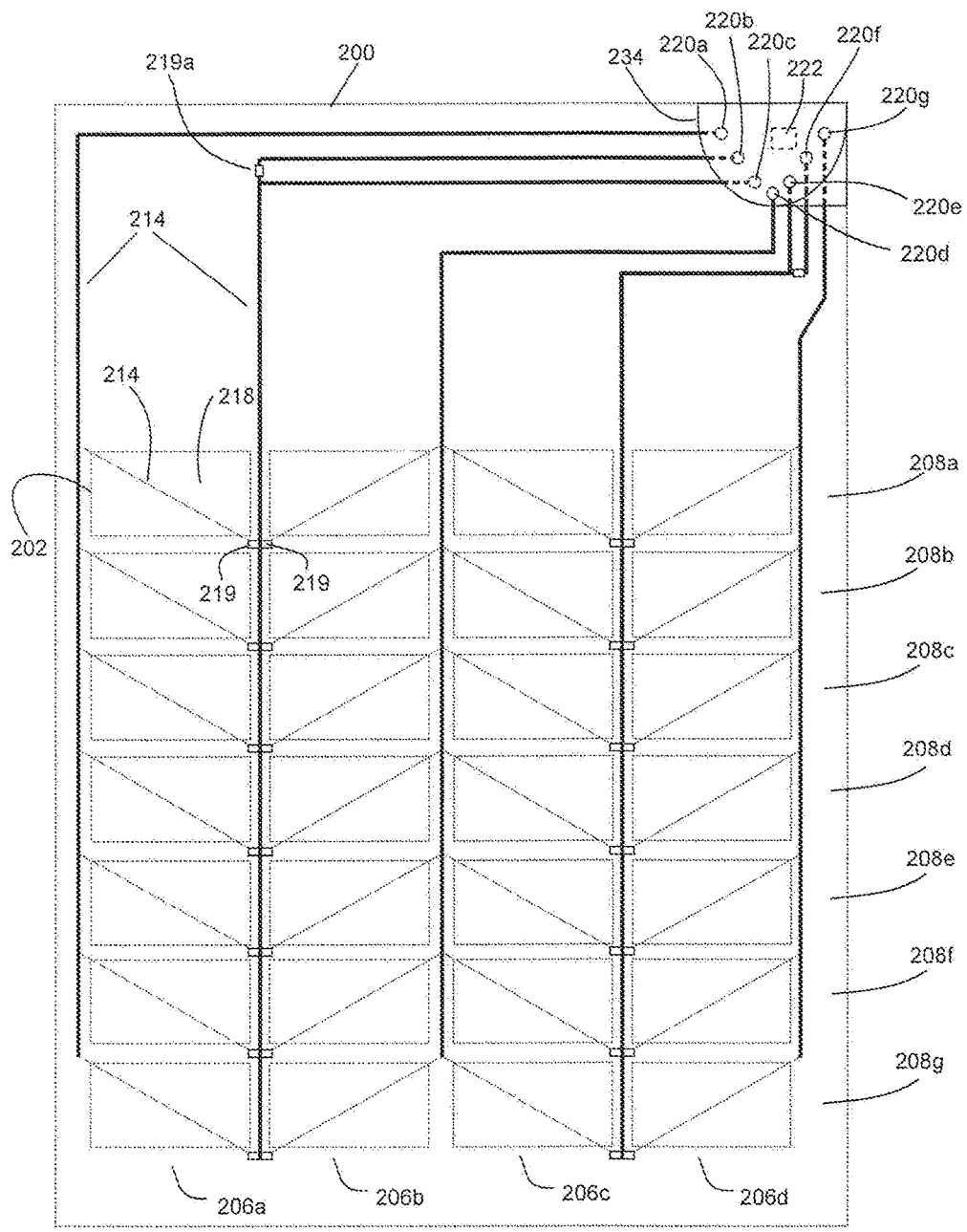
FIG. 18 is an alternate embodiment of the invention.

Referring to FIG. 18, an alternative embodiment of the blister pack 200 comprising blisters 202 and controller module 234 is shown. In this embodiment, each subcircuit 218 preferably comprises a conductive trace 214 and a circuit element 219 extending across it. The circuit elements 219 can include resistors, capacitors, or inductors. In addition, conductive traces 214 extend from the pads 220 down the sides of the subcircuits 218. For example, when the subcircuit 218 in column 206*a* and row 208*a* is broken (i.e. the conductive trace 214 is broken), the corresponding circuit element 219 in column 206*a* and row 208*a* stops being part of the subcircuit 218, thereby changing the circuit parameters.

It is possible to determine the exact blisters 202 that have been opened by detecting the circuit parameters of the subcircuits 218. In particular, the values for each of the individual circuit elements 219 (i.e. resistances, capacitances, inductances, etc.) are preferably unique and selected such as to avoid aliasing in the observed outputs such as voltage, time, and frequency.

For example, if the circuit elements 219 are resistors, then by measuring the output voltage across circuit element 219*a*, it is possible to determine which of the blisters 202 are broken in column 206*a*. If there are N blisters 202, there will be $2^N$ possible combinations. The controller 222 can use a lookup table (LUT) approach to decode which of the blisters 202 are broken based on the measured circuit parameters.

In order to reduce the number of possible combinations, it is possible to read multiple subcircuits 218 at a time. For example, it is possible to read the subcircuits 218 in column 206*a* at the same time. Voltage is applied to pad 220*a*, ground is applied to pad 220*b*, and high impedance is applied to pads 220*d*, 220*e*, 220*f*, and 220*g*. Current will flow from pad 220*a* to pad 220*b* through the conductive traces 214 associated with the subcircuits 218 in column 206*a*. If the circuit elements 219 are resistors, then pad 220*c* is measuring the result of voltage divider across circuit element 219*a*. If one or more subcircuits 218 are broken, the circuit parameters are changed, resulting in a voltage change across circuit element 219*a*. When all of the subcircuits 218 are closed (i.e. the blisters 202 are intact), the voltage measured across circuit element 219*a* is highest. As the subcircuits 218 are broken, the parallel resistance of the circuit elements 219 will increase, thereby lowering the voltage across circuit element 219*a*.

Similarly, the subcircuits 218 in column 206*b* can be read. In this case, voltage is applied to pad 220*d*, ground is applied to pad 220*b*, and high impedance is applied to pads 220*a*, 220*e*, 220*f*, and 220*g*. Current flows from pad 220*d* to pad 220*b* and through the subcircuits 218 in column 206*b*. The voltage across circuit element 219*a* is measured.

Similarly, the subcircuits 218 in column 206*c* can be read. In this case, voltage is applied to pad 220*d*, ground is applied to pad 220*f*, and high impedance is applied to pads 220*a*, 220*b*, 220*c*, and 220*g*. Current flows from pad 220*d* to pad 220*f* and through the subcircuits 218 in column 206*c*. The voltage across circuit element 219*b* is measured.

Finally, the subcircuits 218 in column 206*d* can be read. In this case, voltage is applied to pad 220*g*, ground is applied to pad 220*f*, and high impedance is applied to pads 220*a*, 220*b*, 220*c*, and 220*d*. Current flows from pad 220*g* to pad 220*f* and through the subcircuits 218 in column 206*d*. The voltage across circuit element 219*b* is measured.

It is also possible to use capacitors or inductors instead of resistors for the circuit elements 219. For example, if capacitors are used, it is possible to measure the total capacitance of the subcircuit 218 by measuring the time it takes for the capacitors to charge up to a selected voltage level. Precise time measurements using microcontroller counters enable detecting slight differences in circuit parameters, thereby allowing the determination of which precise subcircuit 218 has been broken.

Figure 19:
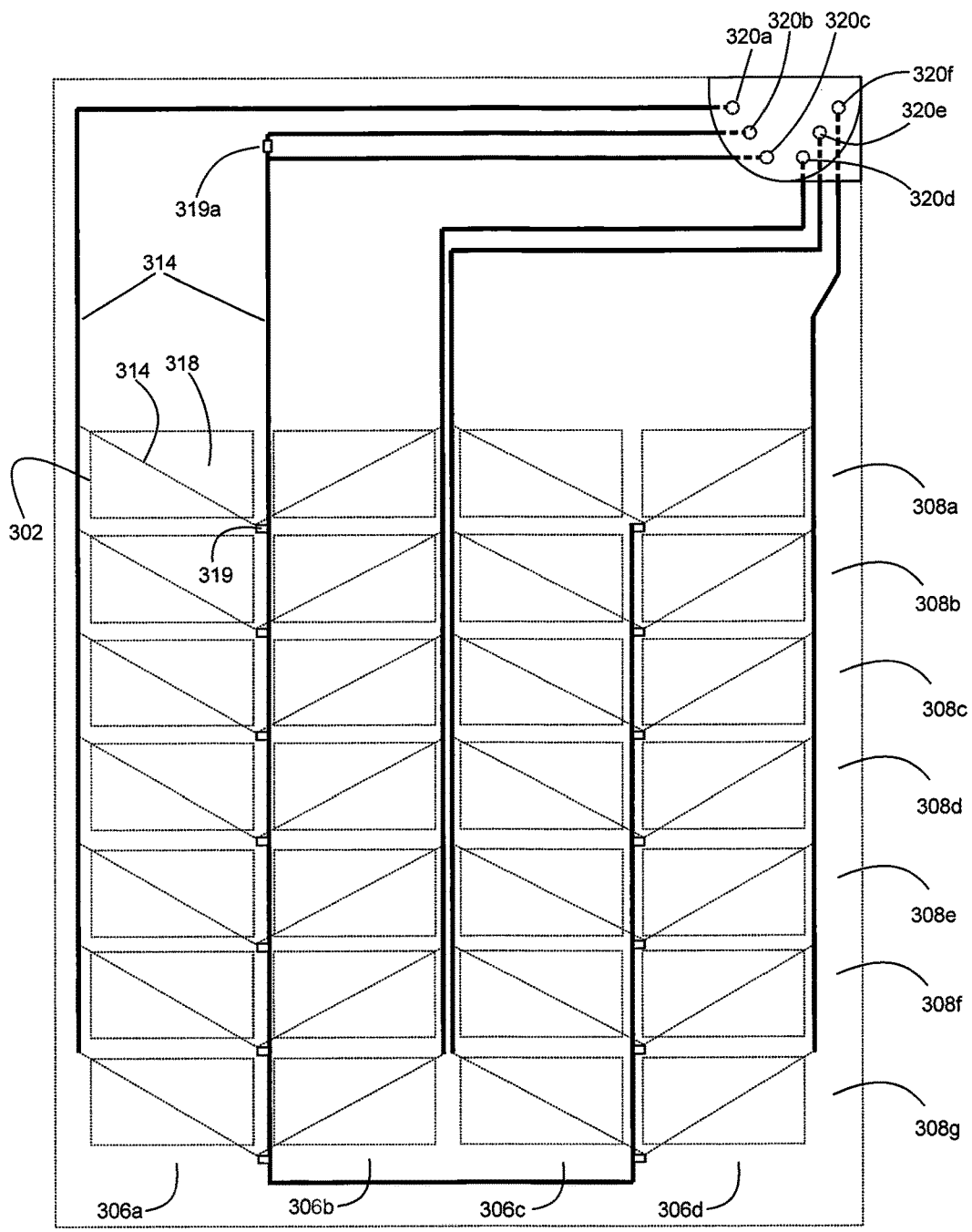
FIG. 19 is another alternate embodiment of the invention.

It is also possible to reduce the number of traces 212, pads 220, and circuit elements 219 used. As shown in FIG. 19, in the blister pack 300 of this embodiment, adjacent subcircuits 318 share the same circuit element 319, resulting in the number of circuit elements 319 required being approximately halved. The conductive traces 314 for both of the subcircuits 318 are electrically connected to the same side of the shared circuit element 319. In order to do so, it may be necessary to have one of the conductive traces 314 for one subcircuit 318 cross over one the conductive traces 314 extending down the sides. Insulating material should be used in this cross-over region in order to avoid a short. Such insulating material may include paper, stickers, glue, etc. In addition, one of the pads 320 can be removed.

Reading the subcircuits 318 in blister pack 300 is as follows. In order to read the subcircuits 318 in column 306a, voltage is applied to pad 320a, ground is applied to pad 320b, and high impedance is applied to pads 320d, 320e, and 320f. Current will flow from pad 320a to pad 320b through the conductive traces 314 associated with the subcircuits 318 in column 306a. The voltage across circuit element 319a is measured.

In order to read the subcircuits 318 in column 306b, voltage is applied to pad 320d, ground is applied to pad 320b, and high impedance is applied to pads 320a, 320e, and 320f. Current will flow from pad 320d to pad 320b. Because high impedance has been applied at pads 320a, 320e, and 320f, the shared circuit elements 319 affect only those subcircuits 318 in column 306b. The voltage across circuit element 319a is measured.

In order to read the subcircuits 318 in column 306c, voltage is applied to pad 320e, ground is applied to pad 320b, and high impedance is applied to pads 320a, 320d, and 320f. Current will flow from pad 320e to pad 320b. Because high impedance has been applied at pad 320a, 320d, and 320f, the shared circuit elements 319 affect only those subcircuits 318 in column 306c. The voltage across circuit element 319a is measured.

Finally, in order to read the subcircuits 318 in column 306d, voltage is applied to pad 320f, ground is applied to pad 320b, and high impedance is applied to pads 320a, 320d, and 320e. Current will flow from pad 320f to pad 320b. Because high impedance has been applied at pads 320a, 320d, and 320e, the shared circuit elements 319 affect only those subcircuits 318 in column 306d. The voltage across circuit element 319a is measured.

Figure 20:
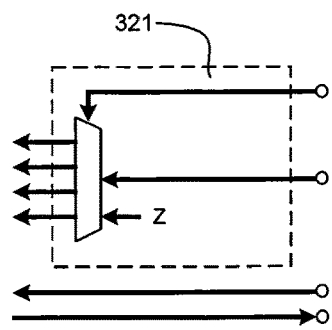
FIG. 20 shows a multiplexer chip in accordance with an embodiment of the invention.

It is also possible to further reduce the number of pads 320 required by using a multiplexer (mux) chip 321. The mux chip 321 can be located on the backing 310 or on some other location on the blister pack 300. The mux chip 321 can aggregate at least a portion of the pads 320 to which voltage was previously applied. Referring to FIG. 20, an example of such a mux chip 321 is shown. The mux chip 321 can output voltage to one of the pads 320, while applying high impedance to the other pads 320.

Figure 21:
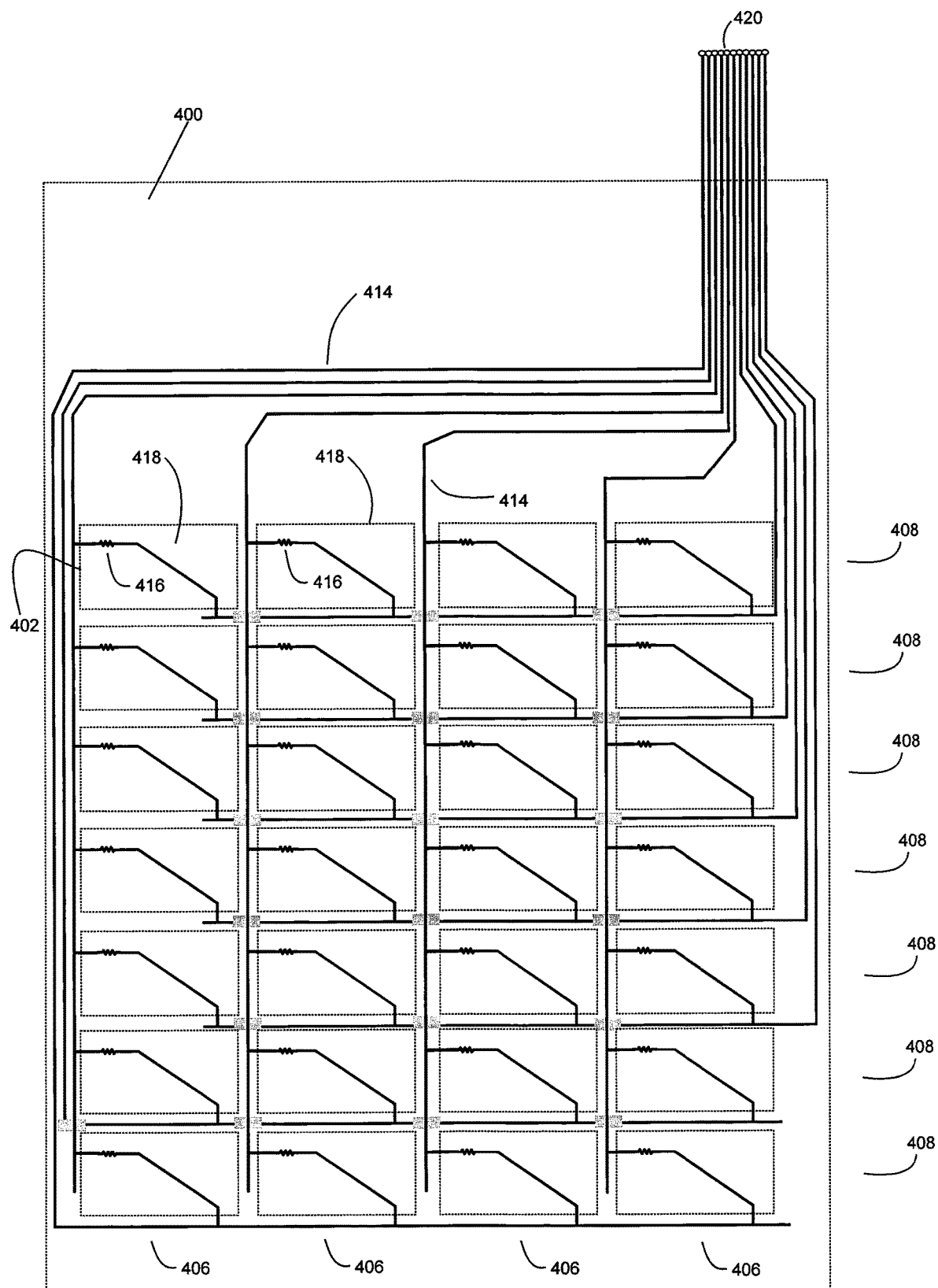
FIG. 21 is another alternative embodiment of the invention.

Referring to FIG. 21, an alternative embodiment of the blister pack 400 is shown. In this embodiment, each subcircuit 418 is associated with at least one resistive trace 416. Eleven pads 420 are provided, with conductive traces 414 extending from each of the pads 420. One conductive trace 414 corresponds to each of the four columns 406 (i.e. one conductive trace 414 is electrically connected to each of the subcircuits 418 in one particular column 406, for a total of four such conductive traces 414). Similarly, one conductive trace 414 corresponds to each of the seven rows 408 (i.e. one conductive trace 414 is electrically connected to each of the subcircuits 418 in one particular row 408, for a total of seven such conductive traces 414).

The arrangement shown in FIG. 21 is for a blister pack 400 containing twenty-eight blisters 402. For blister packs 400 containing a different number of blisters 402, the exact number of conductive traces 414 will be different.

In order to determine whether the blisters 402 have been broken, the subcircuits 418 for the blisters 402 are read one at a time. For example, voltage is applied to one of the columns 406, and the voltage across each of the rows 408 is read. If there is a voltage, then current is going through the subcircuit 418 (i.e. the blister 402 is intact). If instead, there is no voltage, then the subcircuit 418 is broken (i.e. the blister 402 is broken). In order to reduce the effects of ghost current, the pads 420 corresponding to the rows 408 that are not being read can be set to ground.

The resistive traces 416 may all be of the same or similar resistance. For example, each subcircuit 418 may comprise a resistive trace 416 having a resistance of approximately 10 kΩ. However, other resistances may also be used.

Figure 22:
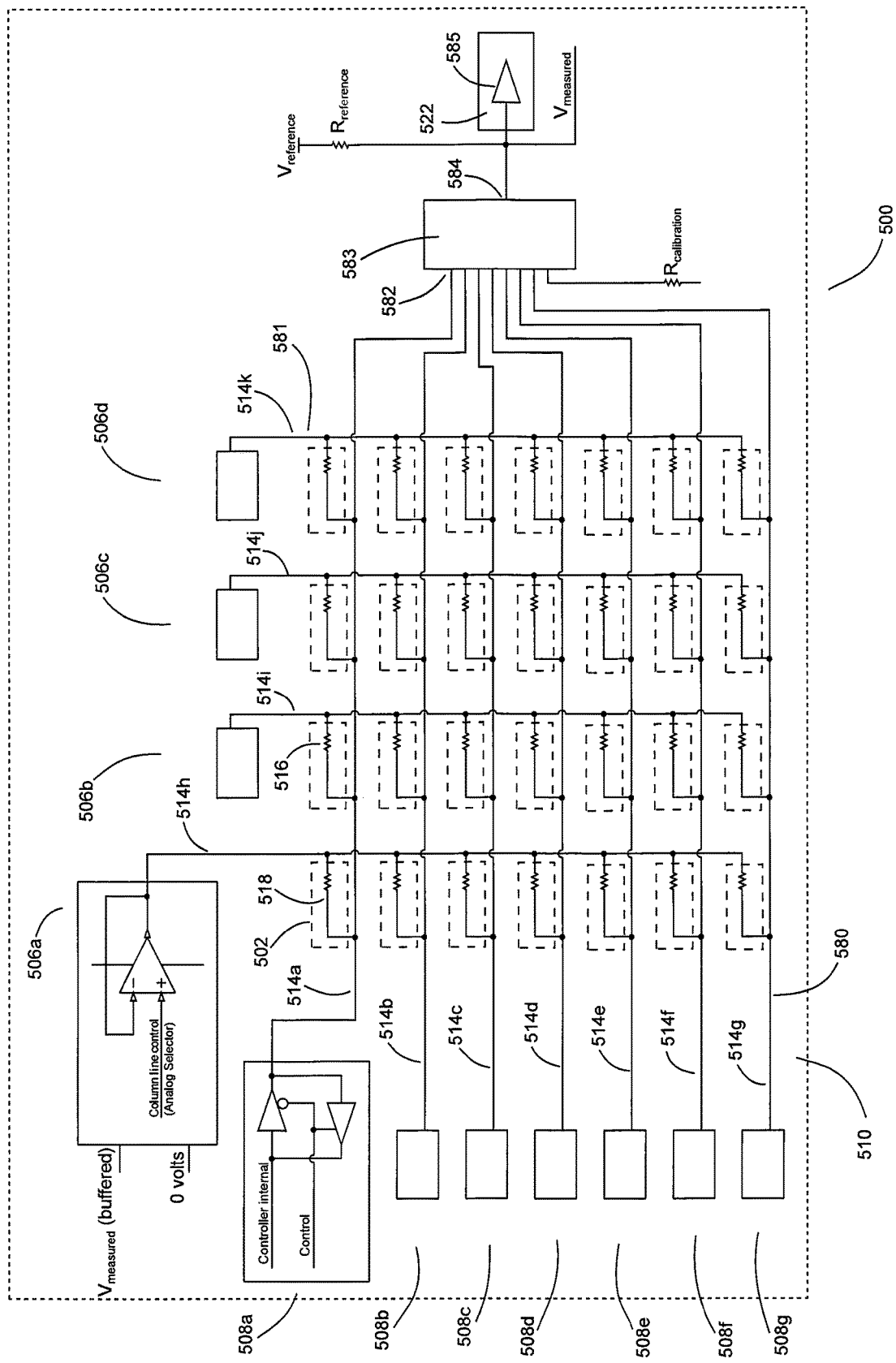
FIG. 22 is a further embodiment of the embodiment of FIG. 21.
Figure 23:
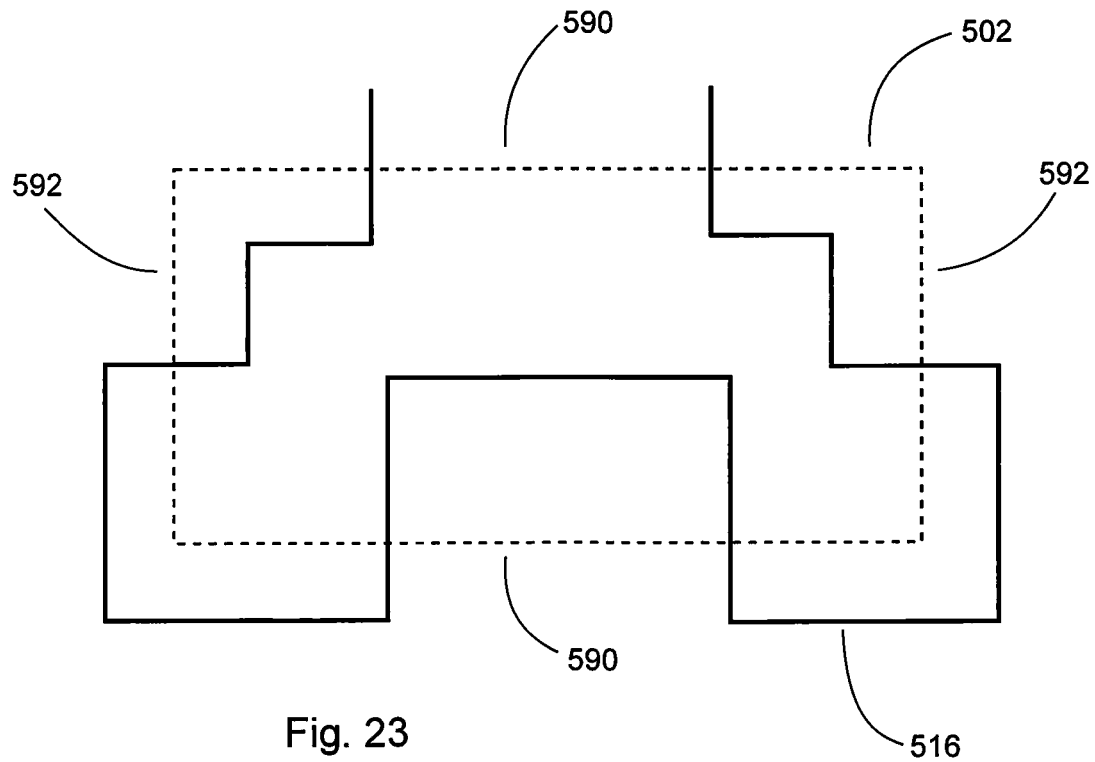
FIG. 23 shows an arrangement of the resistive trace for a blister.
Figure 24:
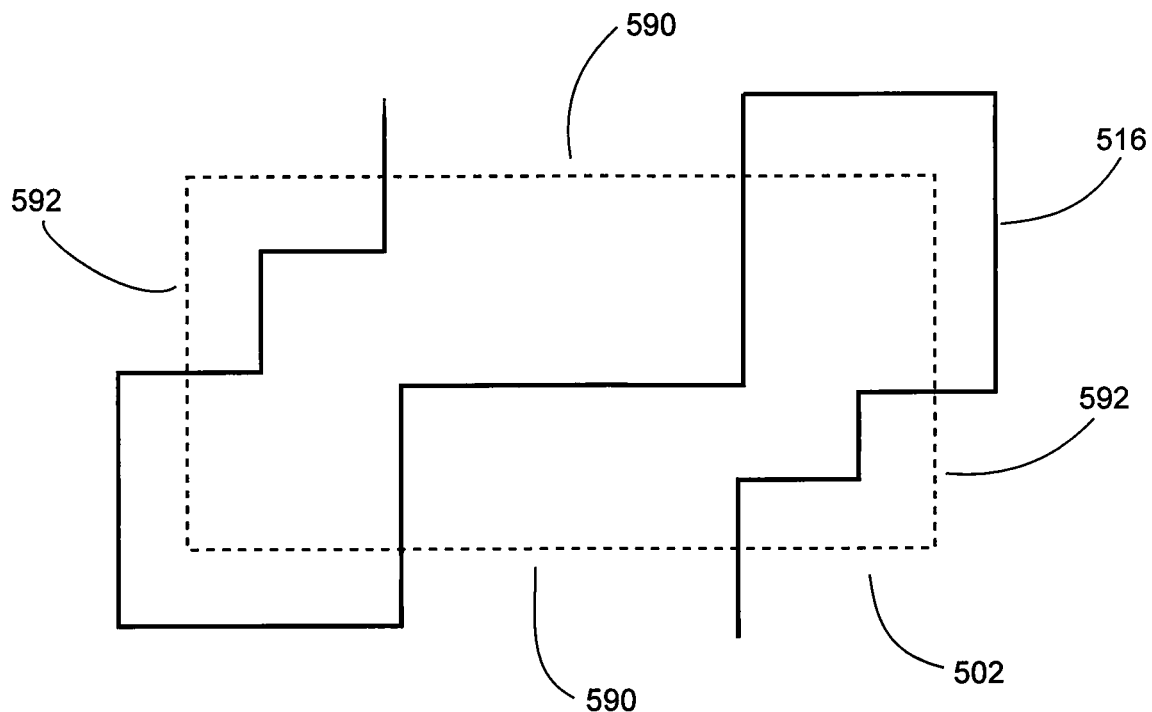
FIG. 24 shows another arrangement of the resistive trace for a blister.

FIG. 22 shows a diagram of a further embodiment of blister pack 500. In this embodiment, the blister pack 500 comprises one or more blisters 502 (shown in dotted line) formed on substantially flat backing 510. The blisters 502 may be arranged generally in a grid of four columns 506 (i.e. columns 506a-506d) and seven rows 508 (i.e. 508a-508g), as shown in FIG. 22. However, it is understood that other numbers of blisters 502 and other arrangements of the blisters 502 may also be used.

The blister pack 500 further comprises a plurality of conductive traces 514 and breakable resistive traces 516, both applied to the backing 510. The conductive traces 514 are arranged into first and second sets 580, 581. Each of the conductive traces 514 in the first set 580 is generally associated with one of the rows 508. Each of the conductive traces 514 in the second set 581 is generally associated with one of the columns 506. Therefore, in the embodiment shown in FIG. 22, there would be a total of 11 conductive traces 514 (i.e. conductive traces 514a-514k), one for each of the four columns 506 and one for each of the seven rows 508. In other words, conductive traces 514a-514g would be part of the first set 580, while conductive traces 514h-514k would be part of the second set 581.

As shown in FIG. 22, all of the blisters 502 in a particular row 508 are therefore associated with a particular conductive trace 514 from the first set 580. For example, all of the blisters 502 in row 508b are associated with conductive trace 514b. Similarly, all of the blisters 502 in a particular column 506 would be associated with one particular conductive trace 514 from the second set 581. For example, all of the blisters 502 in column 506c would be associated with conductive trace 514j. In this manner, each of the blisters 502 would be associated with one conductive trace 514 from the first set 580 and one conductive trace 514 from the second set 581.

Each of the blisters 502 is also associated with one or more resistive traces 516. Preferably, each of the blisters 502 is preferably located on top of its associated one or more resistive traces 516. The one or more resistive traces 516 associated with each of the blisters 502 form subcircuits 518, with each blister 502 being associated with one such subcircuit 518. In the embodiment shown in FIG. 22, the subciruit 518 comprises only one resistive trace 516; however, it is understood that in other embodiments, more than one resistive trace 516 may be connected together to form more complicated circuitry.

As shown in FIG. 22, for each blister 502, its associated subcircuit 518 connects its associated conductive trace 514 from the first set 580 with its associated conductive trace 514 from the second set 581. For example, the blister 502 located at row 508c and column 506d is associated with conductive traces 514c and 514k. The subcircuit 518 for that blister 502 would connect conductive trace 514c to conductive trace 514k.

When the backing 510 beneath a particular blister 502 is broken, its associated subcircuit 518 would be broken (because of the breakage of the resistive traces 516), such that its associated conductive trace 514 from the first set 580 would no longer be connected with its associated conductive trace 514 from the second set 581. Returning to the example of the blister 502 located at row 508c and column 506d, if the backing 510 under that blister 502 was broken, the connection between conductive trace 514c and 514k proximate to that blister 502 would be broken.

As shown in FIG. 22, the conductive traces 514 are preferably applied to the backing 510 in such a way that they are not directly under any of the blisters 502. This is to prevent breakage of the conductive traces 514 when the backing 510 under one or more of the blisters 502 is broken.

The circuitry associated with column 506a and the circuitry associated with row 508a are shown in enlarged detail in FIG. 22. It is understood that similar circuitry may be used for the remaining columns 506 and rows 508, respectively.

The conductive traces 514 from the first set 580 are connected to inputs 582 of a selector 583, with output 584 of the selector 583 being connected to an analog-to-digital converter (ADC) 585 on controller 522. In order to determine whether one of the blisters 502 (e.g. the blister 502 located at row 508c and column 506d) is open, the following procedure may be used. First, in order to minimize the effect of the alternative conductive paths between column-row pairs, row 508c is selected for testing using the selector 583 such that it is now connected to the controller 522. The other rows 508 (i.e. 508a, 508b, and 508d) are tied to ground (to minimize the effect of the common resistors). Then, column 506d is connected to ground (0 volts), while the other columns 506 are driven to the resulting ADC voltage, effectively isolating all of the columns 506 except for column 506d. Because the resistance associated with the blister 502 will be different depending on whether the associated subcircuit 518 is broken, it will be possible to determine whether the blister 502 is broken by measuring the voltage at the ADC 585. For example, it is possible to determine whether the blister 502 is open by comparing the measured voltage with previously determined values for opened and unopened blisters 502.

Similar steps can be used to test other blisters 502 by selecting the appropriate row 508 and column 506 of the particular blisters 502.

In order to determine which of the blisters 502 in the blister pack 500 are open, it is possible to successively iterate through each of the rows 508, and for each row, to iterate through each of the columns 506. In this manner, each blister 502 can be tested to determine whether it is open. This information may also be stored by the controller 522.

The subcircuits 518 may all be of the same or similar resistance. For example, each subcircuit 518 may comprise a resistive trace 516 having a resistance of approximately 10 kΩ. However, other resistances may also be used.

This embodiment reduces the number of conductive traces 514 required, thus making the design of the circuitry easier. In particular, when a large number of conductive traces 514 are required, it may be difficult to design circuitry on the backing 510 given the minimum trace widths and spacing requirements.

FIGS. 23 to 26 show possible arrangements of the resistive traces 516 relative to the blisters 502. In the arrangements shown in FIGS. 23 to 26, the blister 502 is generally rectangular in shape and is generally defined by two long edges 590 and two short edges 592. In both of the arrangements in FIGS. 23 and 24, the resistive trace 516 crosses each of the long edges 590 at two points a, b and crosses each of the short edges 592 at one point c. Therefore, if the backing 510 under the blister 502 is broken along its edges (i.e. the long edges 590 or the short edges 592), there are 6 possible locations along its edges where the resistive trace 516 may be broken. This would reduce the chance that an open blister 502 does not result in breakage of the resistive trace 516, thereby eluding detection by the controller 522 (i.e. a "false negative").

In cases where the blister 502 has more of a general square configuration, it is also possible to have the resistive trace 516 cross each of the edges 590, 592 at two points.

Figure 25:
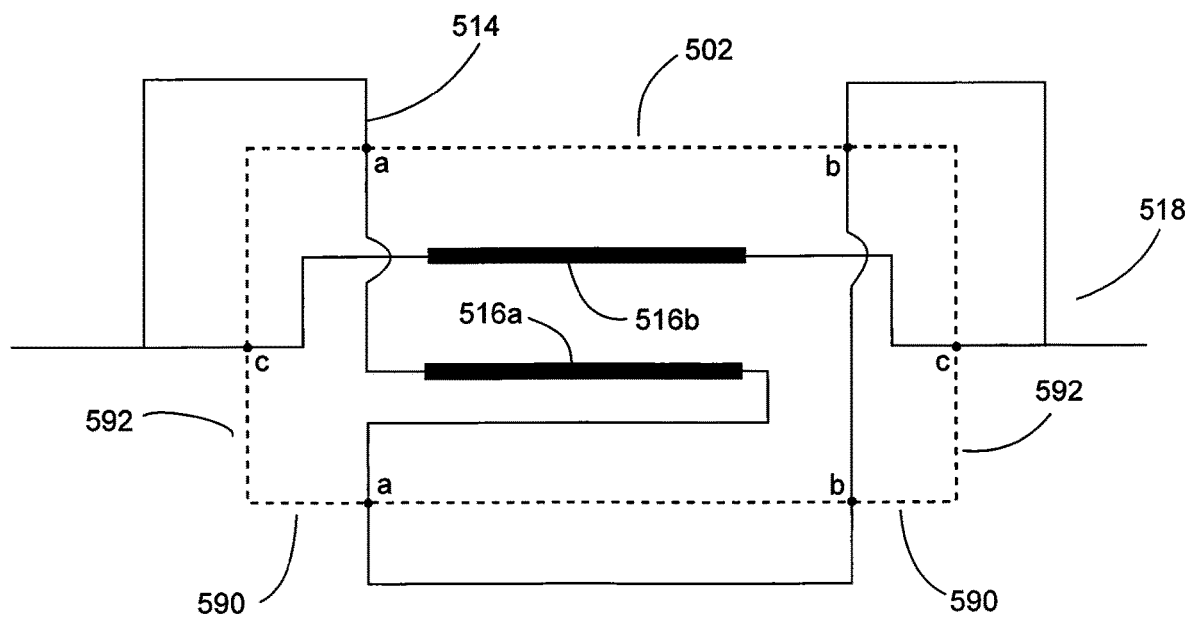
FIG. 25 shows an arrangement of multiple resistive traces for a blister.

On the other hand, in some circumstances, it may be useful to avoid a "false positive" (i.e. where there is an accidental break in the resistive trace 516 but no intended opening of the blister 502). Referring to FIG. 25, a blister 502 and its associated subcircuit 518 is shown. The subcircuit 518 comprises two or more resistive traces 516 connected in parallel. In the arrangement shown in FIG. 25, there are two resistive traces 516 (i.e. 516a, 516b) connected in parallel. The resistive traces 516 in the subcircuit 518 may be connected in parallel using conductive traces 514. In order for the subcircuit 518 to read as broken (thus indicating an open blister 502), it is necessary to break the subcircuit 518 at multiple locations. For example, in the arrangement shown in FIG. 25, the subcircuit 518 crosses each of the long edges 590 at two points a, b and each of the short edges 592 at one point c. In order for subcircuit 518 to be considered broken, the subcircuit 518 must be broken at least at one of points c and at least one of points a, b. In other words, it is necessary to break the subcircuit 518 at least at two or more locations on at least two different edges 590, 592 in order to create an open circuit.

Figure 26:
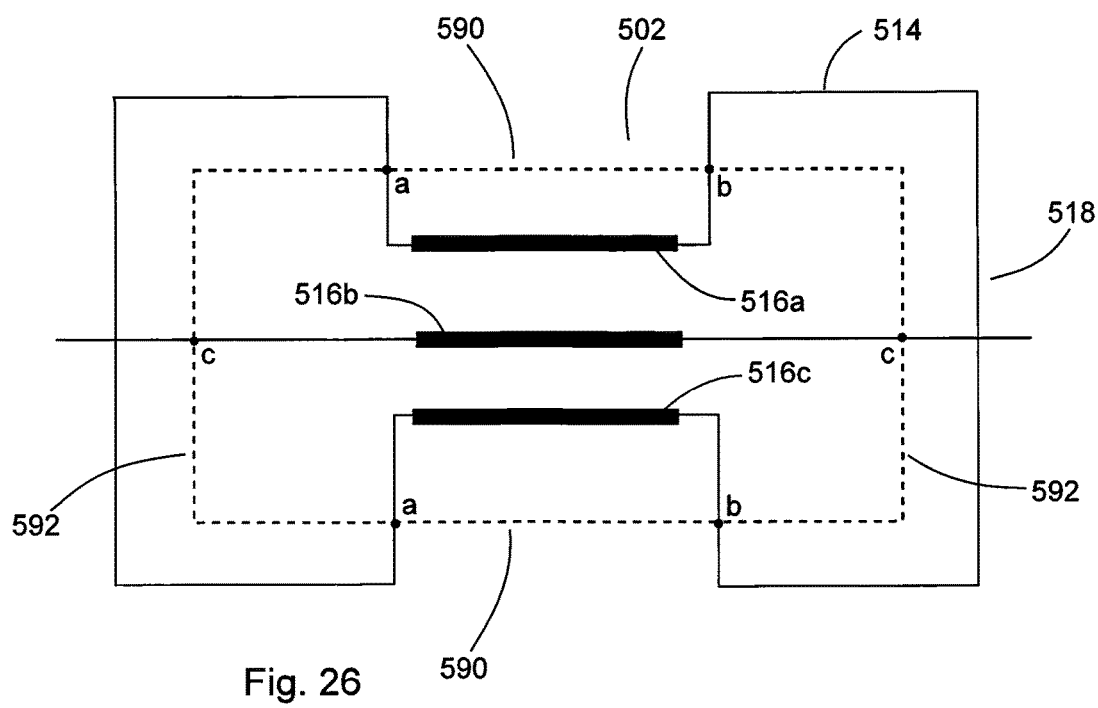
FIG. 26 shows another arrangement of multiple resistive traces for a blister.

FIG. 26 depicts another arrangement of a blister 502 and its associated subcircuit 518. In this arrangement, there are three resistive traces 516 (i.e. 516a, 516b, 516c) connected in parallel. The resistive traces 516 may be connected in parallel using conductive traces 514. Depending on how locations on the subcircuit 518 are broken, the overall resistance of the subcircuit 518 will vary, and this can be used to make a determination as to whether the associated blister 502 should be considered open. In the arrangement shown in FIG. 26, resistive trace 516a is associated with one of the long edges 590, resistive trace 516c is associated with the other of the long edges 590, and resistive trace 516b is associated with the short edges 592. The subcircuit 518 crosses each of the long edges 590 at two points a, b and each of the short edges 590 at one point c. For example, in order to consider the blister 502 open, it may be necessary to have a break on at least two of the long and short edges 590, 592, with at least one of the breaks being on one of the short edges 592.

Figure 27:
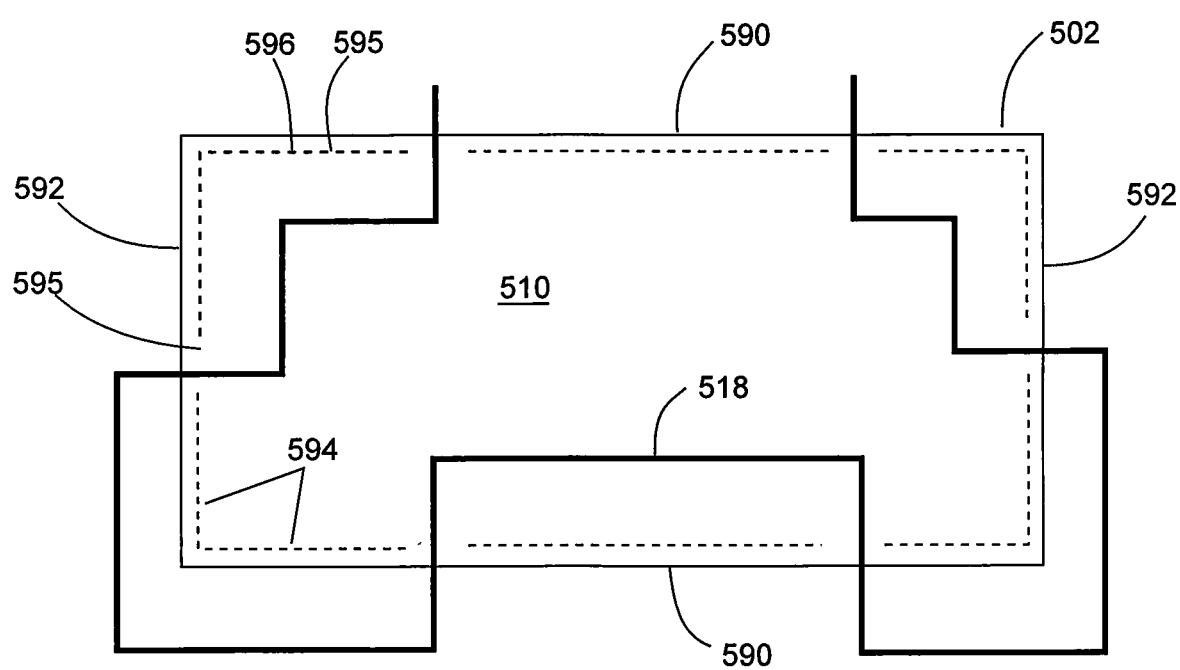
FIG. 27 shows an arrangement of perforations for a blister.

Referring to FIG. 27, the backing 510 may also comprise a perforation perimeter 594 comprising perforations 596 and located proximate to the long and short edges 590, 592 of the blister 502. The perforation perimeter 594 allows for easier rupturing of the backing 510. However, the perforation perimeter 594 preferably comprises a plurality of unperforated gaps 595 between the perforations 596. This provides a balance between making the backing 510 easy to rupture but avoid rupturing the backing 510 (and thus possibly breaking the subcircuits 518) by accident. Preferably, the unperforated gaps 595 are approximately 1.5 mm in width where the perforation perimeter 594 crosses the subcircuit 518 and 0.3 mm elsewhere.

Preferably, the resistive traces 516 are printed on the backing 510 and are generally rectangular in shape. If a larger rectangular shape is used for the resistive traces 516, the printing accuracy is improved. Due to the printing process, the edges of the printed resistive traces 516 are not even or solid, increasing the level of error. However, the edge distortion has a fixed value as measured in millimeters. As a result, the smaller the ratio between the edge distortion size to the overall width of the resistive traces 516, the less error that is caused by the distortion.

It will be appreciated by those skilled in the art that the particular embodiments have been described in some detail but that certain modifications may be practiced without departing from the principles of the invention.

The invention claimed is:

1. A blister pack for dispensing medication, the blister pack comprising:
   a substantially flat backing;
   a plurality of blisters formed on the backing, wherein the blisters and the backing form cavities for containing the medication, wherein the blisters are arranged in a grid comprising rows of blisters and columns of blisters, and wherein each of the blisters is generally defined by a perimeter comprising a plurality of segments;
   a first set of conductive traces applied to the backing, wherein each of the first set of conductive traces is associated with a corresponding one of the rows of blisters such that for each row of associated blisters, one of the first set of conductive traces extends along all of the associated blisters;
   a second set of conductive traces applied to the backing, wherein each of the second set of conductive traces is associated with a corresponding one of the columns of blisters such that for each column of associated blisters, one of the second set of conductive traces extends along all of the associated blisters;
   a plurality of breakable resistive traces applied to the backing, wherein for each blister, at least two of the resistive traces are applied to the backing under the blister to form a subcircuit, wherein the resistive traces in the subcircuit are connected in parallel, wherein each of the resistive traces of the subcircuit is associated with at least one of the segments; and wherein each of subcircuits connects a unique combination of one of the first set of conductive traces and one of the second set of conductive traces; and
   a controller adapted to detect breakage of one or more of the resistive traces under the blisters by successively isolating each of the first set of conductive traces and each of the second set of conductive traces and measuring the voltage across each of either the first set of conductive traces or the second set of conductive traces to compare a difference in the voltage between the blister that is broken and the blister that is unbroken.

2. The blister pack of claim 1, wherein each of the subcircuits has a total resistance, and the total resistance for each of the subcircuits is substantially identical to one other.

3. The blister pack of claim 2, wherein the total resistance is approximately 10 kΩ.

4. The blister pack of claim 1, wherein the plurality of blisters is 28 blisters.

5. The blister pack of claim 1, wherein the rows of blisters are 7 rows of blisters.

6. The blister pack of claim 1, wherein the columns of blisters are 4 columns of blisters.

7. The blister pack of claim 1, further comprising a selector, wherein the selector is adapted to selectively choose one of the first set of conductive traces to input to the controller.

8. The blister pack of claim 1, wherein the controller is further adapted to iteratively determine whether resistive traces under each of the blisters have been broken.

9. The blister pack of claim 1, wherein for each blister, the subcircuit comprises at least three resistive traces connected in parallel.

10. The blister pack of claim 1, wherein the segments comprise two opposed long edges and two opposed short edges.

11. The blister pack of claim 10, wherein the resistive traces cross each of the long edges at least twice and each of the short edges at least once.

12. The blister pack of claim 11, wherein the backing comprises a plurality of perforation perimeters proximate to the perimeters of the blisters, wherein the perforation perimeters each comprise alternating perforations and unperforated gaps, and wherein a first width of the unperforated gap is approximately 1.5 millimeters proximate to where the resistive traces cross either the long edges or the short edges and a second width of the unperforated gap is approximately 0.3 millimeters elsewhere.

13. The blister pack of claim 1, wherein the controller is further adapted to determine, based on comparing the difference in the voltage between the blister that is broken and the blister that is unbroken and based on the association between the segments and the resistive traces, whether one or more of the segments have been broken.

* * * * *